United States Patent
Hong et al.

(10) Patent No.: US 7,247,621 B2
(45) Date of Patent: Jul. 24, 2007

(54) ANTIVIRAL PHOSPHONATE COMPOUNDS AND METHODS THEREFOR

(75) Inventors: Zhi Hong, Aliso Viejo, CA (US); Yung-hyo Koh, Irvine, CA (US); Jae Hoon Shim, Irvine, CA (US); Jean-Luc Girardet, Aliso Viejo, CA (US)

(73) Assignee: Valeant Research & Development, Costa Mesa, CA (US)

( * ) Notice: Subject to any disclaimer, the term of this patent is extended or adjusted under 35 U.S.C. 154(b) by 427 days.

(21) Appl. No.: 10/426,507

(22) Filed: Apr. 29, 2003

(65) Prior Publication Data

US 2004/0023921 A1    Feb. 5, 2004

Related U.S. Application Data

(60) Provisional application No. 60/377,024, filed on Apr. 30, 2002.

(51) Int. Cl.
*A61K 31/70* (2006.01)
*A61K 31/7052* (2006.01)
*C07H 19/04* (2006.01)

(52) U.S. Cl. ............ 514/45; 514/49; 514/50; 514/48; 514/51; 514/43; 536/28.1; 536/28.4; 536/28.5; 536/26.1

(58) Field of Classification Search ............. 514/49, 514/25, 44, 50, 45, 48, 51, 43; 536/27.1, 536/28.1, 28.4, 28.5, 28.53, 25.53, 26.1

See application file for complete search history.

(56) References Cited

U.S. PATENT DOCUMENTS

| | | | |
|---|---|---|---|
| 5,142,051 A | 8/1992 | Holy et al. | |
| 5,208,221 A | 5/1993 | Kim et al. | |
| 5,302,585 A | 4/1994 | Yu et al. | |
| 5,356,886 A | 10/1994 | Harnden et al. | |
| 6,444,837 B1 | 9/2002 | McKenna et al. | |
| 6,495,521 B2 | 12/2002 | Horwitz | |
| 6,812,219 B2 * | 11/2004 | LaColla et al. | 514/49 |

FOREIGN PATENT DOCUMENTS

| | | |
|---|---|---|
| WO | WO 01/90121 | 11/2001 |
| WO | WO 02/054425 | 7/2002 |
| WO | WO/02/057425 A2 | 7/2002 |
| WO | WO 02/100354 | 12/2002 |

OTHER PUBLICATIONS

Moriguchi et al. (Journal of the Chemical Society, Perkin Transactions 1: Organic and Bio-Organic Chemistry (1999), (13), 1859-1865) (Abstract Sent).*
Raju et al. (Journal of Medicinal Chemistry (1989), 32 (6), 1307-13) (Abstract Sent).*
Wnuk et al. (Journal of the American Chemical Society (1996), 118 (10), 2519-20) (Abstract Sent).*
Savochkina LP, et al. Mol. Biol. (Mosk) 1989 23(6) 1700-1710 (Article in Russian); English abstract at p. 1710.
G.A. Freeman et al., J. Med. Chem. 1992, 35, 3192-3196.
G. A. Freeman, et al., "3'-Azido-3',5'-dideoxythymidine-5'-methylphosphonic acid diphosphate: synthesis and HIV-1 reverse transcriptase inhibition.," J. Med. Chem., vol. 35 (No. 17), p. 3192-3196.
L.P. Savochkina, et al., "," Molecular Biology, p. 1700-1710, (Jul. 24, 1989).

* cited by examiner

*Primary Examiner*—Shaojia Anna Jiang
*Assistant Examiner*—Michael C. Henry
(74) *Attorney, Agent, or Firm*—Thelen Reid Brown Raysman & Steiner LLP

(57) ABSTRACT

Pharmaceutical compositions comprise a nucleotide analog with a phosphonate group at a concentration effective to act as a substrate and/or inhibitor of a viral polymerase, and especially of the HCV RNA dependent RNA polymerase.

16 Claims, 12 Drawing Sheets

ANTIVIRAL PHOSPHONATE COMPOUNDS AND METHODS THEREFOR

This application claims the benefit of U.S. provisional application No. 60/377,024, filed Apr. 30, 2002, which is incorporated herein by reference.

FIELD OF THE INVENTION

The field of the invention is pharmaceuticals, and especially those comprising nucleotide analogs.

BACKGROUND OF THE INVENTION

HCV infection poses a significant public health problem worldwide and is recognized as the major cause of non-A, non-B hepatitis. The etiologic agent of hepatitis C, the hepatitis C virus (HCV) is widely regarded as a member of the Flaviviridae family and category of arboviruses, having a single-stranded positive-sense RNA genome encoding a polyprotein of approximately 3000 amino acids.

Although HCV infection resolves itself in some cases, the virus establishes chronic infection in up to 80% of the infected individuals, and may persist for decades. It is estimated that about 20% of these infected individuals will go on to develop cirrhosis, and 1 to 5% will develop liver failure and hepatocellular carcinoma (Seeff, et al. 1999, *Am. J. Med*. 107:10S-15S; Saito, et al. 1990, *Proc. Natl. Acad. Sci. USA*, 87:6547-6549; WHO, 1996, *Weekly Epidemiol. Res.*, 71:346-349). Chronic hepatitis C is the leading cause of chronic liver disease, and the leading indication for liver transplantation in the United States. The Centers for Disease Control and Prevention estimate that hepatitis C is currently responsible for approximately 8,000 to 10,000 deaths in the United States annually. This number is projected to increase significantly over the next decade. Unfortunately, development of effective and safe vaccines for HCV has been impeded by the relatively high immune evasion, probably due to a comparably high degree of heterogeneity of this virus. Still further, mechanistic studies of HCV replication have been hindered by the lack of an in vitro cell culture system and a validated small animal model as an alternative to the chimpanzee.

Currently, the most widely prescribed HCV antiviral therapy is the combination of interferon-alpha 2b (IFN-alpha-2b, Intron A) and ribavirin, a treatment capable of suppressing viral titers in about 40% of chronically infected patients. However, immunogenicity and relatively low serum half-life times of interferon-alpha 2b have limited treatment success, at least in some patients. To overcome at least some of the difficulties with immunogenicity and relatively low serum half-life time, interferon-alpha 2b has been coupled to polyethylene glycol. Use of such modified (pegylated) interferon in HCV therapy has significantly improved the clinical outcome for numerous patients. However, there is still a significant portion of patients in which viral propagation persists, even when Ribavirin is coadministered with pegylated interferon.

Alternative proposed and experimental pharmaceutical compositions for treatment of HCV infections include various nucleoside analogs. Exemplary compositions are described in WO 01/90121 to Novirio, WO 02/57425 to Merck, or WO 02/100354 to Ribapharm. While some of these compositions may have an antiviral effect to at least some degree, various disadvantages remain. Among other things, selectivity of such compounds for the viral polymerase may be less than desirable. Other potential disadvantages may include poor phosphorylation to the corresponding nucleotide (or nucleotide analog).

Furthermore, certain phosphonate nucleoside analogs are known to exhibit significant and selective antiviral effect. For example, 9-(2-Phosphonylmethoxyethyl)adenine (PMEA) is a potent antiviral agent against the hepatitis B virus (see e.g., U.S. Pat. Nos. 4,659,825, 4,724,233 or 4,808,716). However, PMEA is also extremely toxic and therefore has failed to provide a viable drug. In another example, 3'-Azido-3',5'-dideoxythymidine-5'-methylphosphonic acid diphosphate showed promising antiviral effects against the human immunodeficiency virus (HIV), but exhibited relatively poor selectivity and is generally difficult to administer, specifically to infected cells (see e.g., *J. Med. Chem*. 1992 Aug. 21;.35 (17):3192-6). Still further, Watanabe et al. describe in published U.S. Patent Application US 20020055483 selected 2',3'-substituted nucleosides that may include a phosphonate moiety as therapeutic molecules for treatment of hepatitis B, C, and D, or proliferative disorders. However, they report only a therapeutic effect against HBV. In still further known examples, (see e.g., U.S. Pat. Nos. 5,142,051, 5,302,585, 5,208,221, or 5,356,886) various acyclic phosphonate nucleoside analogs are presented with various pharmacological effects. However, such compounds are frequently difficult to synthesize and/or exhibit less than desirable (if any) antiviral activity against HCV.

In yet further examples, inorganic phosphonates (e.g., Foscarnet) have been employed to treat HBV infection as described in U.S. Pat. No. 6,495,521 to Horwitz, while various pyrophosphate analogs were shown to exhibit antiviral effect as described by McKenna et al in U.S. Pat. No. 6,444,837. However, despite relatively promising antiviral activity of such compounds against certain viruses, inorganic phosphonates and pyrophosphate analogs appear to exhibit less than desirable (if any) antiviral activity against HCV.

Therefore, although various compounds and methods are known in the art to treat HCV infection, all or almost all of them suffer from one or more disadvantages. Consequently, there is still a need for improved compounds and methods to treat viral infections, and particularly HCV infections.

SUMMARY OF THE INVENTION

The present invention is generally directed to compositions and methods of treatment of HCV infections, and particularly relates to nucleotide analogs having a phosphonate moiety and pharmaceutical compositions comprising the same.

In one especially preferred aspect, contemplated compositions include a nucleotide analog having a structure according to Formula 1 or 2 (substituents defined as in the section "Contemplated Compounds" below), wherein the nucleotide analog is present in the composition effective to inhibit a viral polymerase of an HCV virus and/or to act as a substrate for the viral polymerase of the HCV virus.

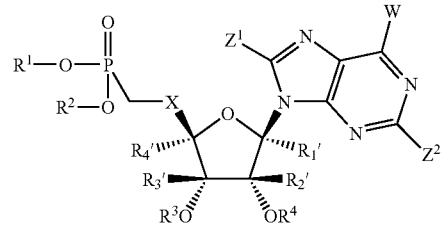

Formula 1

-continued

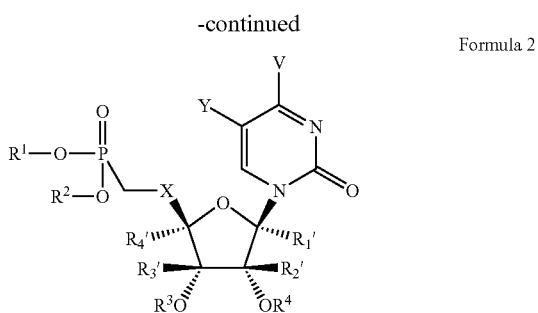

Formula 2

Further preferred nucleotide analogs particularly include those in which X is a covalent bond between the C4'-atom of the sugar and the carbon atom in the phosphonate group, O, or $CH_2$, and wherein at least one of $R_1'$, $R_2'$, $R_3'$, and $R_4'$ is $CH_3$. With respect to heterocyclic bases, it is preferred that $Z_1$ and $Z_2$ is H, and W is $NR^5R^6$, and that Y is H or $CH_3$, and V is OH or $NR^5R^6$. It is still further contemplated that the viral polymerase is disposed in a cell infected with HCV, and most preferably that the cell is disposed in a patient infected with HCV.

In another aspect of the inventive subject matter, prodrugs of the nucleotide analog are contemplated, and particularly preferred prodrugs include a moiety that is preferentially removed from the prodrug in a hepatocyte. Exemplary preferred moieties are covalently bound to the phosphonate group and comprise an amino acid, or form a cyclic group with the phosphonate group. Alternatively, or additionally, pharmaceutically acceptable salts of the nucleotide analogs according to the inventive subject matter are contemplated.

Various objects, features, aspects and advantages of the present invention will become more apparent from the following detailed description of preferred embodiments of the invention and the accompanying drawing.

DETAILED DESCRIPTION

Figure 1:
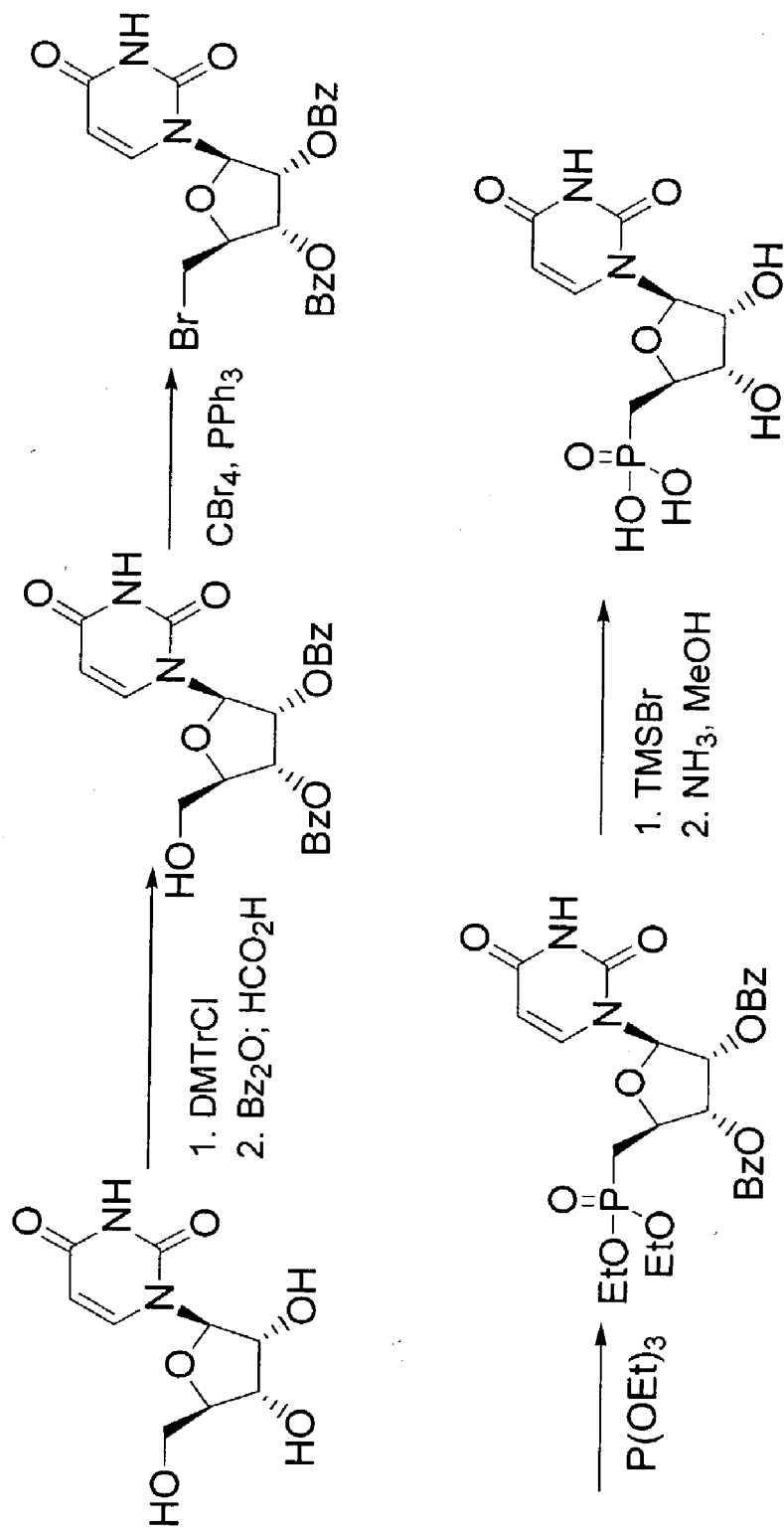
FIG. 1 depicts one contemplated route for the synthesis of exemplary 5'-deoxy-5'-phosphonate nucleosides.

The term "nucleoside" as used herein refers to all compounds in which a heterocyclic base is covalently coupled to a sugar. The term "nucleoside analog" as used herein refers to a nucleoside in which at least one of the sugar and the heterocyclic base is a non-naturally occurring sugar and/or heterocyclic base. An especially preferred coupling of the base to the sugar is a C1'-(glycosidic) bond, in which the C1' carbon atom of the sugar is covalently linked to a carbon- or heteroatom (typically nitrogen) in the base. The term "nucleotide" as used herein refers to a nucleoside that is coupled to a phosphate group (or modified phosphate group, including phosphonate, hytdroxymethylphosphonate, etc.), preferably via the C4'- or C5'-atom. The terms "nucleoside", "nucleotide", "nucleoside analog", and "nucleotide analog" are also employed broadly herein to include all prodrug compositions that are activated or converted in a human to a nucleoside or nucleotide (or analog thereof) in one or more than one step, which step(s) may occur intracellularly or extracellularly. Especially contemplated prodrug forms include those that confer a particular specificity towards a diseased or infected cell or organ. Exemplary contemplated prodrug forms are described in "Prodrugs" by Kenneth B. Sloan (Marcel Dekker; ISBN: 0824786297), "Design of Prodrugs" by Hans Bundgaard (ASIN: 044480675X), and in copending U.S. application Ser. No. 09/594410, filed Jun. 16, 2000. Further preferred prodrugs are found in the section entitled "Contemplated Compounds" below.

The term "alkyl" as used herein refers to any linear, branched, or cyclic, primary, secondary, or tertiary hydrocarbon in which all carbon-carbon bonds are single bonds. This term specifically includes methyl, ethyl, propyl, isopropyl, cyclopropyl, butyl, isobutyl, tertiobutyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term "alkyl" also specifically includes both substituted and unsubstituted alkyls, e.g., where a substituent is a functional group. Particularly contemplated functional groups include nucleophilic (e.g., —$NH_2$, —OH, —SH, —NC, etc.) and electrophilic groups (e.g., C(O)OR, C(X)OH, etc.), polar groups (e.g., —OH), ionic groups (e.g., —$NH_3^+$), and halogens (e.g., —F, —Cl), and all chemically reasonable combinations thereof.

The term "lower alkyl" is used herein and, unless otherwise specified, refers to a $C_1$ to $C_4$ saturated linear, branched, or cyclic (for example cyclopropyl), alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The terms "alkenyl" and "unsubstituted alkenyl" are used interchangeably herein and refer to any linear, branched, or cyclic alkyl with at least one carbon-carbon double bond. The term "substituted alkenyl" as used herein refers to any alkenyl that further comprises a functional group, and particularly contemplated functional groups include those discussed above. The terms "alkynyl" and "unsubstituted alkynyl" are used interchangeably herein and refer to any linear, branched, or cyclic alkyl or alkenyl with at least one carbon-carbon triple bond. The term "substituted alkynyl" as used herein refers to any alkynyl that further comprises a functional group, and particularly contemplated functional groups include those discussed above.

The terms "aryl" and "unsubstituted aryl" are used interchangeably herein and refer to any aromatic cyclic alkenyl or alkynyl. The term "substituted aryl" as used herein refers to any aryl that further comprises a functional group, and particularly contemplated functional groups include those discussed above. The term "alkaryl" is employed where the aryl is further covalently bound to an alkyl, alkenyl, or alkynyl.

The term "protected" as used herein and unless otherwise defined refers to a group that is covalently coupled to an oxygen, nitrogen, or phosphorus atom to prevent further reaction or for other purposes. A wide variety of oxygen, nitrogen, and phosphorus protecting groups are known to those skilled in the art of organic synthesis.

The terms "purine", "deazapurine", "pyrimidine", "imidazole" or "triazole base" include adenine, guanine, hypoxanthine, 2,6-diaminopurine, 6-chloropurine, $N^6$-alkylpurines, $N^6$-acylpurine (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-hydroxyalkyl purine, $N^6$-thioalkyl purine, $N^2$-alkyl purines, $N^2$-alkyl-6-thiopurines, thymine, cytosine, 5-fluorocytosine, 5-methylcytosine, 6-azapyrimidine, including 6-azacytosine, 2-and/or 4-mercaptopyrimidine, uracil, 5-halouracil, including 5-fluorouracil, $C^5$-alkylpyrimidine, $C^5$-benzylpyrimidine, $C^5$-halopyrimidine, $C^5$-vinylpyrimidine, $C^5$-acetylenic pyrimidine, $C^5$-acylpyrimidine, $C^5$-hydroxyalkyl pyrimidine, $C^5$-amidopyrimidine, $C^5$-cyanopyrimidine, $C^5$-nitropyrimidine, $C^5$-aminopyrimidine, 5-azacytosine, 5-azauracil, triazolopyrimidine, imidazolopyrimidine, pyrrolopyrimidine, pyrazolopyrimidine, triazolopyridine, imidazolopyridine, pyrrolopyridine and pyrazolopyridine, $C^4$-carbamoyl imidazole, $C^3$-cyano-1,2,4-triazole, $C^3$-carbamoyl-1,2,4-triazole, $C^3$-carboxamidine-1,2,4-triazole. Functional oxygen and nitrogen groups on the base can be protected as necessary or desired. Suitable protecting groups are well known to those skilled in the art, and include trimethylsilyl, dimethylhexylsilyl, tert-butyldimethylsilyl, and tert-butyldiphenylsilyl, trityl, alkyl groups, and acyl groups such as acetyl and propionyl, methanesulfonyl, and para-toluenesulfonyl.

Still further, the terms "halo" and "halogen" are used interchangeably herein and include chloro, bromo, iodo, and fluoro.

The term "substantially free of" or "substantially in the absence of" refers to a nucleoside phosphonate composition that includes at least 85% or 90% by weight, preferably 95% to 98% by weight, and even more preferably 99% to 100% by weight, of the designated isomer (e.g., D-isomer or L-isomer) of that nucleoside phosphonate. In a preferred aspect of the inventive subject matter, in the methods and compounds of this invention, the compounds are D-isomers and substantially free of the corresponding L-isomer.

Contemplated Compounds

The inventors discovered that various nucleoside analogs, their salts and prodrugs may be employed as inhibitors and/or substrates for a non-mammalian polymerase, and especially as inhibitors of viral and bacterial polymerases, wherein particularly contemplated viral polymerases include RNA-dependent RNA polymerases (which may be de novo polymerases), and most particularly the HCV polymerase NS5B.

Furthermore, the inventors contemplate that contemplated phosphonates and their prodrugs may enter a cell and will be—after intracellular phosphorylation—converted to their diphosphate derivatives. Therefore, it is especially contemplated that nucleoside phosphonate diphosphates (nucleoside triphosphate mimics) may be employed by an RNA-dependent RNA polymerase (and preferably the HCV polymerase) as a nucleotide for incorporation into viral RNA.

In one particularly preferred aspect, contemplated nucleotides and nucleotide analogs will have a structure according to the general formula:

P-X-S-Base wherein P includes a phosphonate (or modified phosphonate, including a phosphoamidate group) that is coupled to a sugar S via a bond, atom, or group X. Further coupled to the sugar S is a heterocyclic base "Base". Thus, contemplated compounds preferbaly comprise a nucleotide in which a phosphonate group or modified phosphonate group is covalently coupled to the sugar of the nucleotide via a group other than a phosphate ester, and wherein the nucleotide is at least one of a substrate and an inhibitor of a viral polymerase.

Preferred phosphonate groups include those that are modified with a cleavable moiety, wherein cleavage is preferably achieved intracellularly by one or more enzymes. Consequently, particularly preferred modified phosphonate groups include moieties covalently coupled to the phosphonate as those described in U.S. Pat. No. 6,312,662 to Erion, which is incorporated by reference herein.

Examples of compound with these preferred phosphonate groups modified with a cleavable moiety include prodrugs having a sturcture according to Formula 1 or 2, wherein $R^1$ and $R^2$ together are

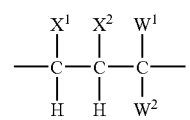

wherein:
$X^1$, $W^1$, and $W^2$ are independently selected from the group consisting of H, alkyl, aralkyl, alicyclic, aryl, substituted aryl, heterosaryl, substituted heteroaryl, 1-alkenyl, and 1-alkynyl; or together $X^1$ and $X^2$ are connected via an additional 3-5 atoms to form a cyclic group containing 5-7 atoms, optionally 1 heteroatom, substituted with hydroxy, acyloxy, alkoxycarbonyloxy, or aryloxycarbonyloxy attached to a carbon atom that is three atoms from both O groups attached to the phosphorous; or together $X^1$ and $X^2$ are connected via an additional 3-5 atoms to form a cyclic group, optionally containing 1 heteroatom that is fused to an aryl group at the beta and gamma position to the O attached to the phosphorous; or together $X^1$ and $W^1$ are connected via an additional 3 carbon atoms to form optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from an O attached to the phosphorous; or together $X^2$ and $W^1$ are connected via an additional 3-5 atoms to form a cyclic group, optionally containing one heteroatom, and $X^1$ must be aryl, substituted aryl, heteroaryl, or substituted heteroaryl; or together $W^1$ and $W^2$ are connected via an additional 2-5 atoms to form a cyclic group, optionally containing 0-2 heteroatoms, and $X^1$ must be aryl, substituted aryl, heteroaryl, or substituted heteroaryl; wherein $X^2$ is selected from the group consisting of —$CHR^{12}OH$, —$CHR^{12}OC(O)R^{13}$, —$CHR^{12}OC(S)R^{13}$, —$CHR^{12}OC(S)OR^{13}$, —$CHR^{12}OC(O)SR^{13}$, —$CHR^{12}OCO_2R^{13}$, —$OR^{12}$, —$SR^{12}$, —$CHR^{12}N_3$, —$CH_2aryl$, —$CH(aryl)OH$, —$CH(CH=CR^{12}_2)OH$, —$CH(C\equiv CR^{12})OH$, —$R^{12}$, —$NR^{12}_2$, —$OCOR^{13}$, —$OCO_2R^{13}$, —$SCOR^{13}$, —$SCO_2R^{13}$, —$NHCOR^{12}$, —$NHCO_2R^{13}$, —$CH_2NHaryl$, —$(CH_2)_p$—$OR^{14}$, and —$(CH_2)_p$—$SR^{14}$;

p is 2 or 3;

$R^{12}$ is selected from the group consisting of $R^{13}$ and —H;

$R^{13}$ is selected from the group consisting of alkyl, aryl, alicyclic, and aralkyl; and $R^{14}$ is selected from the group consisting of —H and lower acyl.

Preferred sugars have the general formula of $C_nH_{2n}O_n$, wherein n is between 2 and 8, and where applicable, the sugar is in the D- or L-configuration. Moreover, it should be appreciated that there are numerous equivalent modifications of such sugars known in the art (sugar analogs), and all such modifications are specifically included herein. For example, some contemplated alternative sugars will include sugars in which the heteroatom in the cyclic portion of the sugar is an atom other than oxygen (e.g., sulfur, carbon, or nitrogen) analogs, while other alternative sugars may not be cyclic but in a linear (open-chain) form. Suitable sugars may also include one or more double bonds. Still further specifically contemplated alternative sugars include those with one or more non-hydroxyl substituents, and particularly contemplated substituents include mono-, di-, and triphosphates (preferably as $C_5'$ esters), alkyl groups, alkoxy groups, halogens, amino groups and amines, sulfur-containing substituents, etc.

Particularly contemplated modifications include substituted ribofuranoses, wherein the substituent is a substituent (preferably in beta orientation) on the 2'- and/or 3'-carbon atoms, most preferably an alkyl, alkenyl, alkynyl, aryl, heterocycle, $CF_3$, $CF_2H$, $CCl_3$, $CCl_2H$, $CH_2OH$, CN, COOR', and CONHR', with R' being $C_{1-10}$ alkyl, alkenyl, alkynyl, aryl. However, it should be appreciated that all contemplated substituents (hydroxyl substituents and non-hydroxyl substituents) may be directed in the alpha or the beta position.

Numerous contemplated sugars and sugar analogs are commercially available. Where contemplated sugars are not commercially available, it should be recognized that there are various methods known in the art to synthesize such sugars. For example, suitable protocols can be found in "Modern Methods in Carbohydrate Synthesis" by Shaheer H. Khan (Gordon & Breach Science Pub; ISBN: 3718659212), in U.S. Pat Nos. 4,880,782, and 3,817,982, and in WO88/00050, or in EP199,451.

Similarly, contemplated heterocyclic bases preferably comprise a heterocyclic base that can form at least one hydrogen bond to another heterocyclic base in a (oligo- or poly-) nucleoside or (oligo- or poly-) nucleotide. Consequently, contemplated heterocyclic bases include compounds in which a plurality of atoms (wherein at least one atom is an atom other than a carbon atom) form a ring via a plurality of covalent bonds. However, particularly contemplated heterocyclic bases have between one and three rings, wherein especially preferred rings include 5- and 6-membered rings with nitrogen, sulfur, or oxygen as the non-carbon atom (e.g., imidazole, pyrrole, triazole, dihydropyrimidine). Further contemplated heterocycles may be fused (i.e., covalently bound) to another ring or heterocycle, and are thus termed "fused heterocycles" as used herein. Especially contemplated fused heterocycles include a 5-membered ring fused to a 6-membered ring (e.g., purine, pyrrolo[2,3-d]pyrimidine), and a 6-membered ring fused to another 6-membered or higher ring (e.g., pyrido[4,5-d]pyrimidine, benzodiazepine).

Preferred groups X of the general formula provided above will include all atoms/groups that replace the C5'-carbon of the sugar in the nucleotide (analog) with a methylene group (which may or may not be substituted, and preferably halogenated), an oxygen atom, a sulfur atom, or a covent bond (thus forming a bond between the C4'-atom of the sugar and the carbon atom in the phosphonate group).

In one preferred aspect, compounds of Formulae (I)-(IV) or pharmaceutically acceptable salts or prodrugs thereof are contemplated

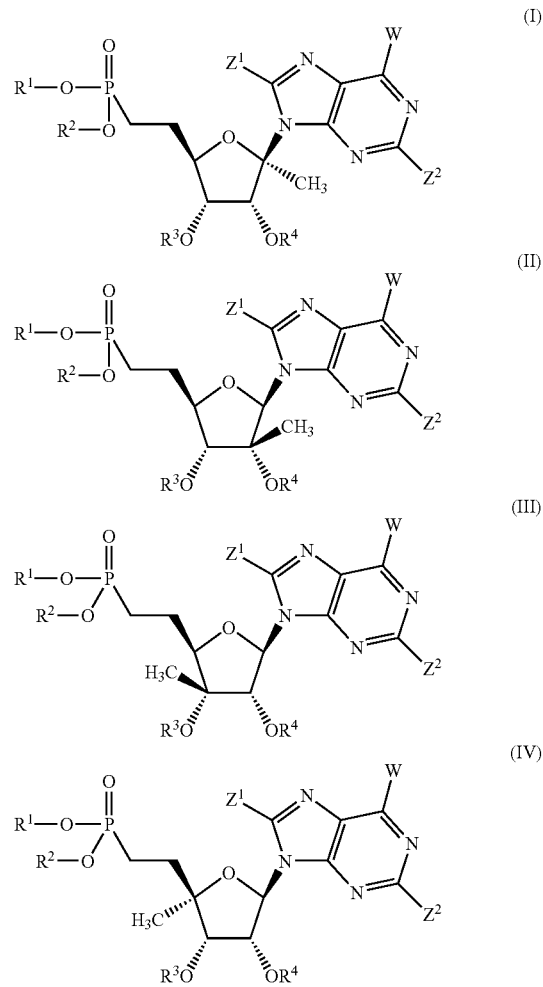

wherein $R^1$ and $R^2$ are independently H, phosphate, diphosphate, or a group that is preferentially removed in a hepatocyte to yield the corresponding OH group. The term "preferentially removed in a hepatocyte" as used herein means at least part of the group is removed in a hepatocyte at a rate higher than the rate of removal of the same group in a non-hepatocytic cell (e.g., fibroblast or lymphocyte). It is therefore contemplated that the removable group includes all pharmaceutically acceptable groups that can be removed by a reductase, esterase, cytochrome P450 or any other specific liver enzyme. Alternative contemplated groups may also include groups that are not necessarily preferentially removed in a hepatocyte, but effect at least some accumulation and/or specific delivery to a hepatocyte (e.g., esters with selected amino acids, including valine, leucine, isoleucine, or polyarginine or polyaspartate).

$R^3$ and $R^4$ are independently H, phosphate (including mono-, di- or triphosphate), acyl (especially including lower acyl), alkyl (especially including lower alkyl), sulfonate ester, including alkyl or arylalkyl sulfonyl including methane sulfonyl and benzyl (wherein the phenyl group is optionally substituted with one or more substituents) lipids, including phospholipids, amino acids, carbohydrates, peptides, cholesterol, or another pharmaceutically acceptable leaving group which, when administered in vivo is capable of providing a compound wherein $R^3$ and $R^4$ is H.

W is hydrogen, bromo, chloro, fluoro, iodo, $OR^5$, $NR^5R^6$, $NH(NR^5R^6)$, $N(alkyl)(NR^5R^6)$, CN, $C(O)NR^5R^6$, $C(NH)NR^5R^6$ or $SR^5$; $Z^1$ and $Z^2$ are independently selected from the group consisting of H, alkyl, CO-alkyl, CO-aryl, CO-alkoxyalkyl, chloro, bromo, fluoro, iodo, $OR^5$, $NR^6R^7$ or $SR^5$; and $R^5$ and $R^6$ are independently H, acyl (especially including lower acyl), or alkyl (and especially including methyl, ethyl, propyl and cyclopropyl). In particularly preferred aspects of Formulae (I)-(IV), the compound is in the form of a prodrug or a pharmaceutically acceptable salt thereof, and additionally or alternatively, $Z_1$ and $Z_2$ in contemplated compounds is H, while W is $NR^5R^6$.

In another preferred aspect, compounds of Formulae (V)-(VIII) or pharmaceutically acceptable salts or prodrugs thereof are contemplated

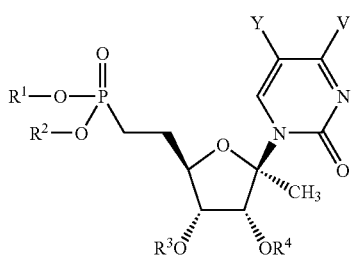

(V)

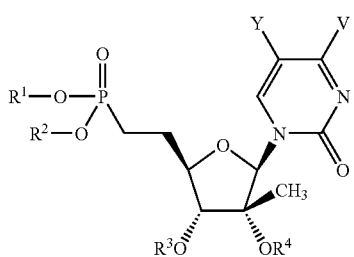

(VI)

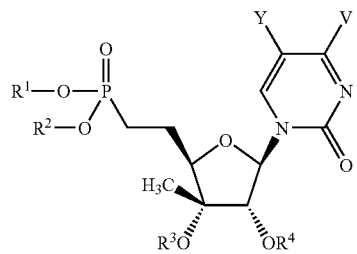

(VII)

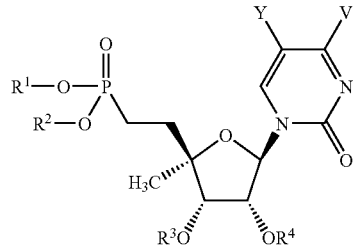

(VIII)

wherein $R^1$ and $R^2$ are independently H, phosphate, diphosphate, or a group that is preferentially removed in a hepatocyte to yield the corresponding OH group. Thus, contemplated groups include all pharmaceutically acceptable groups that can be removed by a reductase, esterase, cytochrome P450 or any other specific liver enzyme. Alternative contemplated groups may also include groups that are not necessarily preferentially removed in a hepatocyte, but effect at least some accumulation and/or specific delivery to a hepatocyte (e.g., esters with selected amino acids, including valine, leucine, isoleucine, or polyarginine or polyaspartate).

$R^3$ and $R^4$ are independently H, phosphate (including mono-, di- or triphosphate), acyl (especially including lower acyl), alkyl (especially including lower alkyl), sulfonate ester, including alkyl or arylalkyl sulfonyl including methane sulfonyl and benzyl (wherein the phenyl group is optionally substituted with one or more substituents) lipids, including phospholipids, amino acids, carbohydrates, peptides, cholesterol, or another pharmaceutically acceptable leaving group which, when administered in vivo is capable of providing a compound wherein $R^3$ and $R^4$ is H.

V is hydrogen, bromo, chloro, fluoro, iodo, $OR^5$, $NR^5R^6$, $NH(NR^5R^6)$, $N(alkyl)(NR^5R^6)$, CN, $C(O)NR^5R^6$, $C(NH)NR^5R^6$ or $SR^5$; Y is H, alkyl, CO-alkyl, CO-aryl, CO-alkoxyalkyl, chloro, bromo, fluoro, iodo, $OR^5$, $NR^6R^7$, or $SR^5$; and $R^5$ and $R^6$ are independently H, acyl (especially including lower acyl), or alkyl (and especially including methyl, ethyl, propyl and cyclopropyl). In particularly preferred aspects of Formulae (V)-(VIII), the compound is in the form of a prodrug or a pharmaceutically acceptable salt thereof, and additionally or alternatively, Y in contemplated compounds is H or $CH_3$, while V is OH or $NR^5R^6$.

Of course, it should be recognized that the compounds of Formulae (I)-(IV) may be prepared such that the C5'-atom of the sugar is replaced by a heteroatom, and most preferably an oxygen atom. Thus, in a further preferred aspect, contemplated compounds may have a structure according to Formulae (IX)-(XII), wherein the substituents $R^1$, $R^2$, $R^3$, $R^4$, V and Y are defined as described for compounds according to Formulae (V)-(VIII) above:

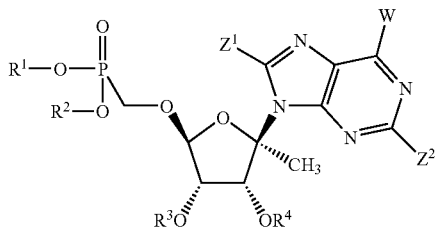

(IX)

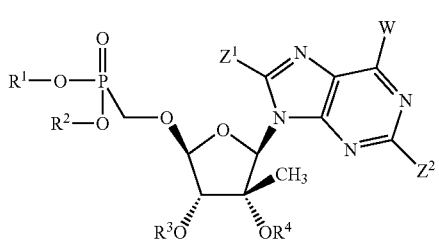

(X)

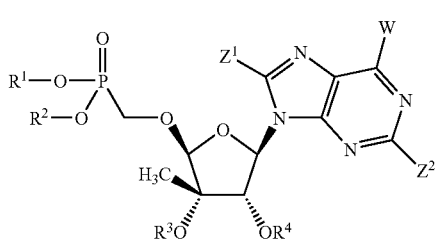

(XI)

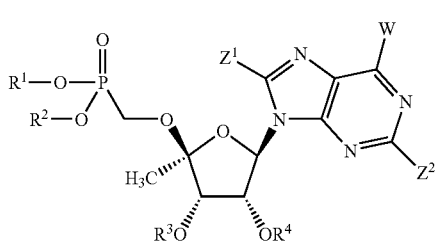

(XII)

Similarly, corresponding modifications (i.e., replacement of C5'-atom with oxygen) may be made for the compounds according to Formulae (V)-(VIII) to provide the compounds according to Formulae (XIII)-(XVI) wherein the substituents $R^1$, $R^2$, $R^3$, $R^4$, $Z^1$, $Z^2$, and W are defined as described for compounds according to Formulae (I)-(IV) above:

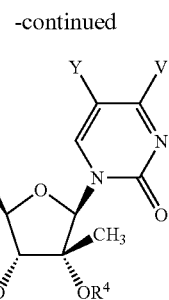

(XIII)

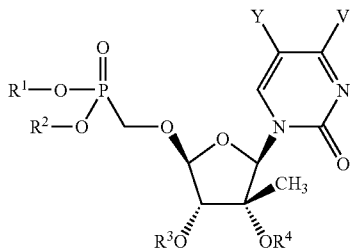

(XIV)

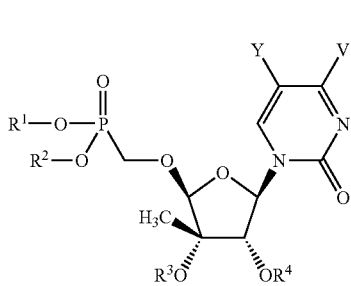

(XV)

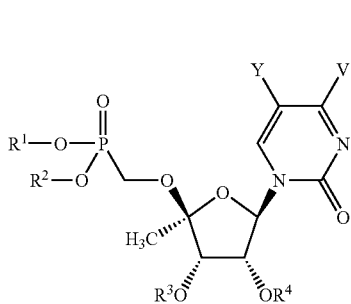

(XVI)

In a still further preferred aspect of the inventive subject matter, contemplated nucleotide analogs may be prepared such that the phosphonate moiety is directly and covalently bound to the C5'-atom of the sugar, or via an alkylene (or other) linker as depicted in the compounds according to Formulae (XVII)-(XIX). Alternatively, or additionally, such compounds may include modified sugar moieties as depicted below.

Here, the heterocyclic bases of the nucleotide analogs include all suitable heterocyclic bases (e.g., substituted purine, deaza purine, pyrimidine, imidazole, or triazole). However, particularly preferred heterocyclic bases especially include those as described in compounds according to Formulae (I) and (V). Consequently, particularly preferred compound will have a general structure according to Formulae (XVII)-(XIX), and may be present in the form of a pharmaceutically acceptable salt or prodrug thereof:

(XVII)

-continued

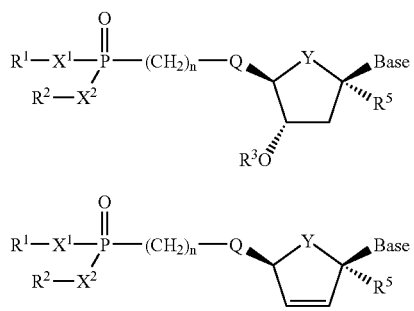

in which n is 0, 1, 2 or 3 (alternatively, one or more $CH_2$ can be replaced by CHF, $CF_2$, CHCl, $CCl_2$, CHBr, $CBr_2$, CH(CN), or CH(alkyl)); $X^1$ and $X^2$ are independently O, S or NH; Q is O or S when n=1, 2 or 3; Q is $CH_2$ when n=0;

$R^1$ and $R^2$ are independently H, phosphate, diphosphate, or a group that is preferentially removed in a hepatocyte to yield the corresponding OH group. Thus, contemplated groups include all pharmaceutically acceptable groups that can be removed by a reductase, esterase, cytochrome P450 or any other specific liver enzyme. Alternative contemplated groups may also include groups that are not necessarily preferentially removed in a hepatocyte, but effect at least some accumulation and/or specific delivery to a hepatocyte (e.g., esters with selected amino acids, including valine, leucine, isoleucine, or polyarginine or polyaspartate).

$R^3$ and $R^4$ are independently H, phosphate (including mono-, di- or triphosphate), acyl (especially including lower acyl), alkyl (especially including lower alkyl), sulfonate ester, including alkyl or arylalkyl sulfonyl including methane sulfonyl and benzyl (wherein the phenyl group is optionally substituted with one or more substituents) lipids, including phospholipids, amino acids, carbohydrates, peptides, cholesterol, or another pharmaceutically acceptable leaving group which, when administered in vivo is capable of providing a compound wherein $R^3$ and $R^4$ is H.

$R^5$ is hydrogen, hydroxy, alkyl (including lower alkyl), alkoxy, azido, cyano, alkenyl, alkynyl, Br-vinyl, 2-Br-ethyl, —C(O)O(alkyl), —C(O)O(lower alkyl), —O(acyl), —O(lower acyl), —O(alkyl), —O(lower alkyl), —S(alkyl), —S(O)(alkyl), —S(O)(O)(alkyl), —O(alkenyl), CF3, CHF2, CH2F, CH2OH, CH2O(lower alkyl), chloro, bromo, fluoro, iodo, $NO_2$, $NH_2$, —NH(lower alkyl), —NH(acyl), —N(lower alkyl)$_2$, —N(acyl)$_2$;

Y is O, S, $SO_2$, C(=$CH_2$), $NR^6$ or $CH_2$; $R^6$ is H, acyl (including lower acyl) or alkyl (including lower alkyl).

In a first preferred aspect of Formulae (XVII)-(XIX), a compound is provided wherein n is 1, Q is O, and the Base is as described in compounds according to Formulae (I) and (V). $R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is alkyl; $X^1$ and $X^2$ are O; and Y is O, S or $CH_2$.

In a second preferred aspect of Formulae (XVII)-(XIX), a compound is provided wherein n is 1, Q is $CH_2$, and the Base is as described in compounds according to Formulae (I) and (V). $R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is alkyl; $X^1$ and $X^2$ are O; and Y is O, S or $CH_2$.

In a third preferred aspect of Formulae (XVII)-(XIX), a compound is provided wherein n is 1, Q is O or $CH_2$, and the Base is as described in compounds according to Formulae (I) and (V). $R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is alkyl; $X^1$ and $X^2$ are O; and Y is O.

Similarly, the $R^5$ substituent (and especially where R5 is a substituent other than H) may also be in a position other than in beta-orientation at the C1'-atom, and where it is preferred that the alternative position is at the C2'-atom, compounds according to Formula (XX)-(XXII) are especially contemplated. With respect to the substituents $R^1$, $R^2$, $X^1$, $X^2$, Q, Y, $R^3$, $R^4$, and $R_5$ and the number n, the same considerations as described above for compounds according to Formulae (XVII)-(XIX) apply.

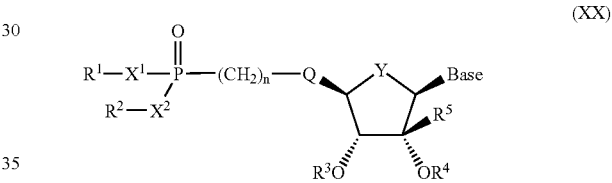

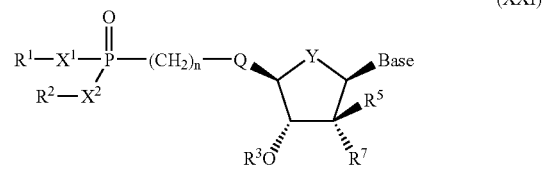

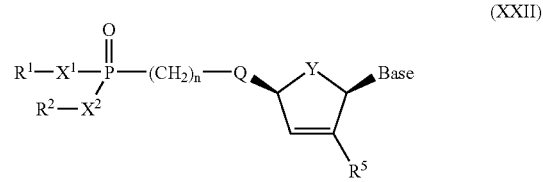

In a first preferred aspect of Formulae (XX)-(XXII), n is 1, Q is O, and the Base is as described in compounds according to Formulae (I) and (V). $R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is alkyl; $X^1$ and $X^2$ are O; and Y is O, S or $CH_2$.

In a second preferred aspect of Formulae (XX)-(XXII), a compound is provided wherein n is 1, Q is $CH_2$, and the Base is as described in compounds according to Formulae (I) and (V). $R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is alkyl; $X^1$ and $X^2$ are O; and Y is O, S or $CH_2$.

In a third preferred aspect, of Formulae (XX)-(XXII), a compound is provided wherein n is 1, Q is O or $CH_2$, and the Base is as described in compounds according to Formulae (I) and (V). $R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is alkyl; $X^1$ and $X^2$ are O; and Y is O.

Furthermore, the $R^5$ substituent (and especially where $R^5$ is a substituent other than H) may also be in a position other than in beta-orientation at the C1'- or C2'-atom, and where it is preferred that the alternative position is at the C3'-atom, compounds according to Formula (XXIII)-(XXV) are especially contemplated. With respect to the substituents $R^1$, $R^2$, $X^1$, $X^2$, Q, Y, $R^3$, $R^4$, and $R^5$ and the number n, the same considerations as described above for compounds according to Formulae (XVII)-(XIX) apply.

group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is alkyl; $X^1$ and $X^2$ are O; and Y is O, S or $CH_2$.

In a third preferred aspect, of Formulae (XXIII)-(XXV), a compound is provided wherein n is 1, Q is O or $CH_2$, and the Base is as described in compounds according to Formulae (I) and (V). $R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is alkyl; $X^1$ and $X^2$ are O; and Y is O.

Still further, the $R^5$ substituent (and especially where R5 is a substituent other than H) may also be the C4'-atom as depicted in compounds according to Formula (XXVI)-(XXVIII). Again, with respect to the substituents $R^1$, $R^2$, $X^1$, $X^2$, Q, Y, $R^3$, $R^4$, and $R^5$ and the number n, the same considerations as described above for compounds according to Formulae (XVII)-(XIX) apply.

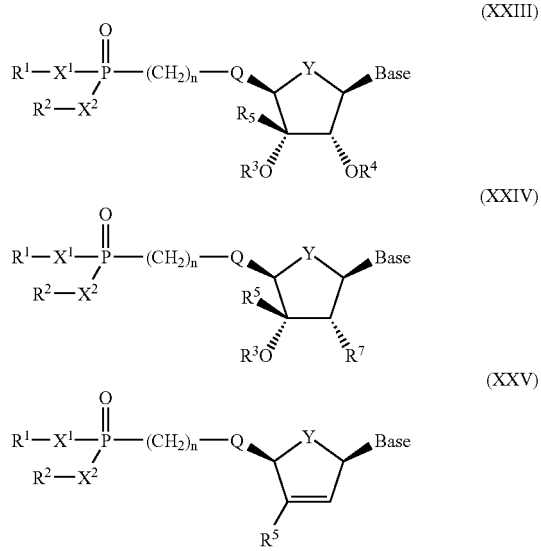

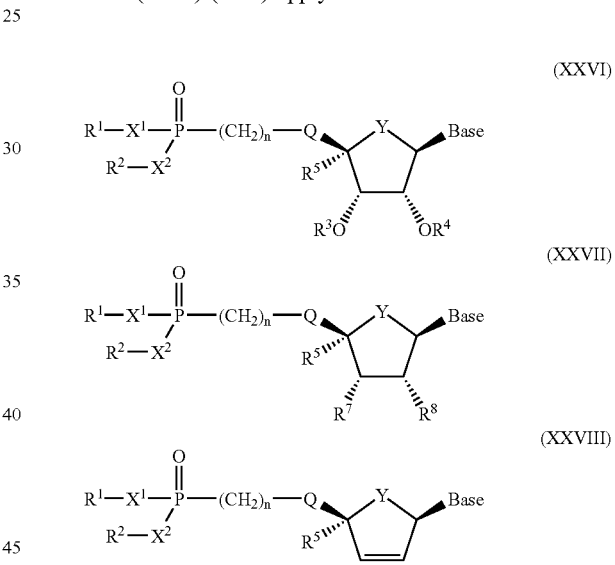

In a first preferred aspect of Formulae (XXIII)-(XXV), a compound is provided wherein n is 1, Q is O, and the Base is as described in compounds according to Formulae (I) and (V). $R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is alkyl; $X^1$ and $X^2$ are O; and Y is O, S or $CH_2$.

In a second preferred aspect of Formulae (XXIII)-(XXV), a compound is provided wherein n is 1, Q is $CH_2$, and the Base is as described in compounds according to Formulae (I) and (V). $R^1$ and $R^2$ are independently H, phosphate (including monophosphate, diphosphate and stabilized phosphate prodrugs) or any pharmaceutically acceptable In a first preferred aspect of Formulae (XXVI)-(XXVIII), a compound is provided wherein n is 1, Q is O, and the Base is as described in compounds according to Formulae (I) and (V). $R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is alkyl; $X^1$ and $X^2$ are O; and Y is O, S or $CH_2$.

In a second preferred aspect of Formulae (XXVI)-(XXVIII), a compound is provided wherein n is 1, Q is $CH_2$, and the Base is as described in compounds according to Formulae (I) and (V). $R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is alkyl; $X^1$ and $X^2$ are O; and Y is O, S or $CH_2$.

In a third preferred aspect of Formulae (XXVI)-(XXVIII), a compound is provided wherein n is 1, Q is O or $CH_2$, and the Base is as described in compounds according to Formulae (I) and (V). $R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is alkyl; $X^1$ and $X^2$ are O; and Y is O.

Finally, the $R^5$ substituent (and especially where R5 is a substituent other than H) may also be bound to the C5'-atom to provide a "branched" sugar as depicted in compounds according to Formulae (XXIX)-(XXXI). Once more, with respect to the substituents $R^1$, $R^2$, $X^1$, $X^2$, Q, Y, $R^3$, $R^4$, and $R^5$ and the number n, the same considerations as described above for compounds according to Formulae (XVII)-(XIX) apply.

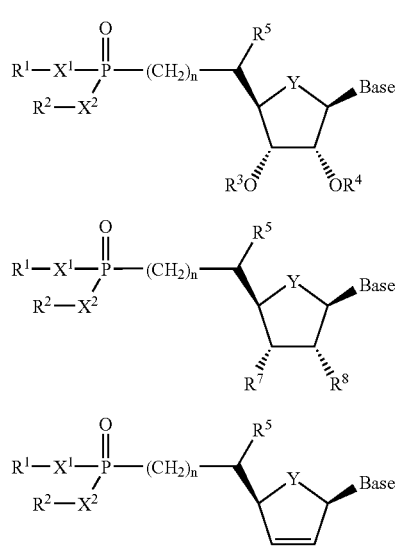

(XXIX)

(XXX)

(XXXI)

In a first preferred aspect of Formulae (XXIX)-(XXXI), a compound is provided wherein n is 0, and the Base is as described in compounds according to Formulae (I) and (V). $R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is H; $X^1$ and $X^2$ are O; and Y is O, S or $CH_2$.

In a second preferred aspect of Formulae (XXIX)-(XXXI), a compound is provided wherein n is 1, and the Base is as described in compounds according to Formulae (I) and (V). $R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is H; $X^1$ and $X^2$ are O; and Y is O, S or $CH_2$.

In a third preferred aspect of Formulae (XXIX)-(XXXI), a compound is provided wherein n is 1, and the Base is as described in compounds according to Formulae (I) and (V). $R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H; $R^3$ and $R^4$ are H; $R^5$ is alkyl; $X^1$ and $X^2$ are O; and Y is O.

In a still further particularly preferred aspect, compounds according to Formulae (XXXII)-(XXXIII), or a pharmaceutically acceptable salt or prodrug thereof, are provided:

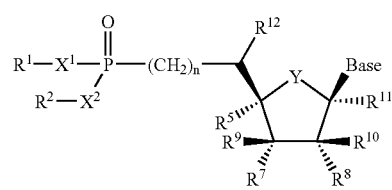

(XXXII)

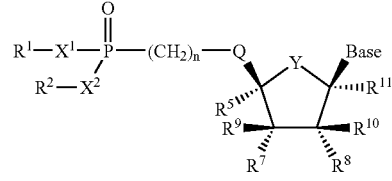

(XXXIII)

wherein n is 0, 1, 2 or 3. Alternatively, one or more $CH_2$ can be replaced by CHF, $CF_2$, CHCl, $CCl_2$, CHBr, $CBr_2$, CH(CN), or CH(alkyl), and the Base is as described in compounds according to Formulae (I) and (V).

$R^1$ and $R^2$ are independently H, phosphate (including monophosphate, diphosphate and stabilized phosphate prodrugs) or any pharmaceutically acceptable group (including groups activated by reductase, esterase, cytochrome or any other liver enzyme) known to undergo a chemical modification resulting in the release of the compound wherein $R^1$ and $R^2$ is an H;

$R^5$, $R^9$, $R^{10}$, $R^{11}$ and $R^{12}$ are independently selected from hydrogen, hydroxy, alkyl (including lower alkyl), alkoxy, azido, cyano, alkenyl, alkynyl, Br-vinyl, 2-Br-ethyl, —C(O)O(alkyl), —C(O)O(lower alkyl), —O(acyl), —O(lower acyl), —O(alkyl), —O(lower alkyl), —S(alkyl), —S(O)(alkyl), —S(O)(O)(alkyl), —O(alkenyl), CF3, CHF2, CH2F, CH2OH, CH2O(lower alkyl), chloro, bromo, fluoro, iodo, $NO_2$, $NH_2$, —NH(lower alkyl), —NH(acyl), —N(lower alkyl)$_2$, —N(acyl)$_2$;

$R^7$ and $R^8$ are independently hydrogen, $OR^3$, hydroxy, alkyl (including lower alkyl), alkoxy, azido, cyano, alkenyl, alkynyl, Br-vinyl, 2-Br-ethyl, —C(O)O(alkyl), —C(O)O(lower alkyl), —O(acyl), —O(lower acyl), —O(alkyl), —O(lower alkyl), —S(alkyl), —S(O)(alkyl), —S(O)(O)(alkyl), —O(alkenyl), CF3, CHF2, CH2F, CH2OH, CH2O(lower alkyl), chloro, bromo, fluoro, iodo, $NO_2$, $NH_2$, —NH(lower alkyl), —NH(acyl), —N(lower alkyl)$_2$, —N(acyl)$_2$; alternatively, $R^7$ and $R^9$, $R^7$ and $R^{10}$, $R^8$ and $R^9$, or $R^8$ and $R^{10}$ can come together to form pi bonds;

Q is O or S when n=1, 2 or 3; Q is $CH_2$ when n=0; $X^1$ and $X^2$ are independently O, S or NH; Y is O, S, $SO_2$, C(=$CH_2$), $NR^6$ or $CH_2$; and $R^6$ is H, acyl (including lower acyl), or alkyl (including lower alkyl).

In yet further contemplated aspects of the inventive subject matter, it is contemplated that the carbon atom of the phosphonate group may be substituted with hydrogen atoms, halogen atoms, and one hydrogen atom and one halogen atom. Thus, contemplated compounds also include halophosphonate nucleotide analogs and a mixed halophosphonate nucleotide analog (i.e., with one hydrogen atom and one halogen atom at the carbon of the phosphonate group).

Moreover, it should be recognized that all prodrugs and metabolites of the compounds according to Formulae (I)-(XXIII) are contemplated. There are numerous prodrug modifications of pharmacologically active molecules known in the art, and all of such modifications are considered suitable for use herein. However, especially preferred prodrugs include those that deliver contemplated compounds to a target cell (e.g., hepatocyte infected with HCV) or target organ (e.g., liver infected with HCV), wherein the prodrug form may be converted within a cell, organ, or other body compartment in an enzymatic or non-enzymatic manner. Especially preferred prodrug forms include those described in WO 99/45016 and various esters with preferably lipophilic amino acids. Further preferred prodrugs particularly include those in which the prodrug form is less active as compared to the corresponding non-prodrug form. Thus, specifically preferred compounds may include a moiety that increases uptake of the prodrug into a cell, or that increases preferential retention of the compound (which may or may not be in prodrug form) in a cell. Alternatively, contemplated compounds may be formulated to increase target specificity of the compound (e.g., organ specific liposomes).

With respect to the metabolite, it should be recognized that metabolites of contemplated compounds might be formed by one or more enzymatic reactions (e.g., via hydrolysis, oxidation, reduction, lyase, or ligase reaction, or even via a polymerase action), or via non-enzymatic reactions (e.g., acid hydrolysis, reduction). For example, a hydrolase or lyase may cleave a portion of contemplated compounds to a more active form. On the other hand, reactions of hydroxylases, ligases, or other enzymes that add chemical groups to the compounds according to the inventive subject matter (to render the compounds more active) are also contemplated herein. Thus, it should be recognized that all metabolites that have a desirable therapeutic effect, and especially an antiviral effect, are deemed suitable.

Contemplated Activity and Uses

The inventors surprisingly discovered that the compounds according to the inventive subject matter inhibit non-mammalian polymerases and/or act as a substrate for non-mammalian polymerases. Particularly contemplated polymerases include viral and bacterial polymerases, and most preferably viral RNA-dependent RNA polymerases (e.g., HCV polymerase NS5B). The term "act as a substrate for the polymerase" as used herein means that the compound is incorporated via a covalent bond into a nascent oligo-or polynucleotide that is synthesized by the polymerase, wherein the compound may then either act as a chain terminator or as a non-chain-terminator (i.e., the compound will form part of a polynucleotide in which the compound is not at the 3'-end of the polynucleotide). Of course it should be recognized that where contemplated compounds act as a substrate, such compounds may be present in diphosphate or triphosphate form (either synthetic, or phosphorylated in vitro or in vivo by a kinase).

Still further, it should be recognized that inhibition of the polymerase may be specific, relative to a mammalian polymerse, and suitable specificities are generally inhibitions that are at least 2-fold, more typically at least 10-fold, and most typically at least 100-fold relative to the mammalian polymerase. The term "inhibit a polymerase" as used herein means reduction of the polymerase activity (e.g., as evidenced by formation of product on a PAGE) of at least 5%, more typically at least 35%, and most typically of at least 90% as compared to the polymerase activity under identical conditions but in the absence of the inhibiting compound.

Consequently, a particularly preferred use of contemplated compounds includes use of such compounds in the treatment of viral diseases, and particularly HCV. Therefore, especially preferred aspects of contemplated compounds include methods and compositions for the treatment of hepatitis C in humans or other host animals in which an effective amount of the contemplated compounds, pharmaceutically acceptable salts or prodrugs thereof are administered, optionally in a pharmaceutically acceptable carrier. Where such compounds are prodrugs, it should be recognized that the prodrugs either possess antiviral (e.g., anti-HCV) activity, or are metabolized to a compound that exhibits such activity.

In an especially preferred use, the inventors contemplate a pharmaceutical composition that includes a nucleotide analog having a structure according to Formula 1 or Formula 2, wherein the nucleotide analog is present in the composition effective to inhibit a viral polymerase of an HCV virus or to act as a substrate for the viral polymerase of the HCV virus

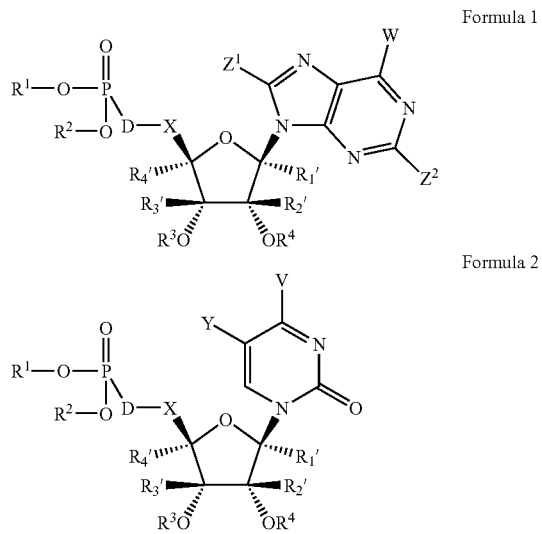

Formula 1

Formula 2 wherein $Z^1$ and $Z^2$ are independently H, alkyl, halogen, $OR^5$, $SR^5$, $NR^5R^6$, CO-alkyl, CO-aryl, or CO-alkoxyalkyl, and wherein W is H, $OR^5$, $SR^5$, $NR^5R^6$, $NH(NR^5R^6)$, $N(alkyl)(NR^5R^6)$, CN, $C(O)NR^5R^6$, $C(NH)NR^5R^6$, or halogen; wherein V is hydrogen, halogen, $OR^5$, $SR^5$, $NR^5R^6$, $NH(NR^5R^6)$, $N(alkyl)(NR^5R^6)$, CN, $C(O)NR^5R^6$, or $C(NH)NR^5R^6$, and wherein Y is H, alkyl, halogen, $OR^5$, $SR^5$, $NR^5R^6$, CO-alkyl, CO-aryl, or CO-alkoxyalkyl; X is a covalent bond between the C4'-atom of the sugar and the carbon atom in the phosphonate group, O, $CH_2$, $CHR^5$, CHHalogen, or $C(Halogen)_2$; D is $CH_2$, CHHalogen, or $C(Halogen)_2$; $R^1$ and $R^2$ are independently H, phosphate, or a group that is preferentially removed in a hepatocyte to yield a corresponding OH group; $R_1'$, $R_2'$, $R_3'$, and $R_4'$ are independently H or alkyl; $R^3$ and $R^4$ are H, or where at least one of $R_1'$, $R_2'$, $R_3'$, and $R_4'$ is alkyl, $R^3$ and $R^4$ are independently H, phosphate, acyl, alkyl, or a group that is preferentially removed in the hepatocyte to a corresponding C2'—OH group or C3'—OH group; $R^5$ and $R^6$ are independently H, alkyl, or acyl.

Where compounds have a structure according to Formula 1, it is particularly preferred that X is a covalent bond between the C4'-atom of the sugar and the carbon atom in the phosphonate group, O, or $CH_2$, and wherein at least one of $R_1'$, $R_2'$, $R_3'$, and $R_4'$ is $CH_3$ (most preferably $R_2'$ is $CH_3$). Alternatively, or additionally $Z_1$ and $Z_2$ is H, and wherein W is $NR^5R^6$. On the other hand, where compounds have a structure according to Formula 2, it is particularly preferred that X is a covalent bond between the C4'-atom of the sugar and the carbon atom in the phosphonate group, O, or $CH_2$, and wherein at least one of $R_1'$, $R_2'$, $R_3'$, and $R_4'$ is $CH_3$ (most preferably $R_2'$ is $CH_3$). Alternatively, or additionally Y is H or $CH_3$, and wherein V is OH, or $NR^5R^6$.

Contemplated compounds can be administered as any salt or prodrug, that upon administration to the recipient is capable of providing directly or indirectly the parent compound, or that exhibits activity itself. Non-limiting examples are the pharmaceutically acceptable salts (alternatively referred to as "physiologically acceptable salts"), and a compound that has been alkylated or acylated at the 5'-position or on the purine or pyrimidine base (a type of "pharmaceutically acceptable prodrug"). Further, the modifications can affect the biological activity of the compound, in some cases increasing the activity over the parent compound. This can easily be assessed by preparing the salt or prodrug and testing its antiviral activity according to the methods described herein or other methods known to those skilled in the art.

Where contemplated nucleosides are administered in a pharmacological composition, it is contemplated that suitable compounds can be formulated in a mixture with a pharmaceutically acceptable carrier. For example, contemplated compounds can be administered orally as pharmacologically acceptable salts, or intravenously in a physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration. In particular, contemplated nucleosides may be modified to render them more soluble in water or other vehicle, which for example, may be easily accomplished by minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient. Thus, and among various other administrations, it is preferred that contemplated pharmaceutical compositions will be administered to a viral polymerase which is disposed in a cell infected with HCV (most typically, the cell is disposed in a patient infected with HCV).

In yet another especially preferred aspect, the active compound can be administered in combination or alternation with another anti-HCV agent, which may be a nucleoside analog (e.g., ribavirin, Viramidine) and/or an interferon (e.g., pegylated IFN-alpha or IFN-gamma). In combination therapy, an effective dosage of two or more agents, are administered together, whereas during alternation therapy an effective dosage of each agent is administered serially. The dosages will depend on absorption, inactivation, and excretion rates of the drugs as well as other factors known to those skilled in the art. It is to be noted that dosage values will also vary with the severity of the condition to be alleviated. It is to be further understood that for any particular subject, specific dosage regimens and schedules should be adjusted over time according to the individual need and the professional judgement of the person administering or supervising the administration of the compositions.

Consequently, methods of treatment of a viral or bacterial infection will include one step in which it is ascertained that the bacterium or virus includes a polymerase that incorporates compounds according to the inventive subject matter into a nascent polynucleotide. In a further step, contemplated compounds are administered to a mammal infected with the virus or bacterium in a dosage effective to inhibit the polymerase. Alternatively, contemplated compounds may be administered to a polymerase in vitro or in vivo at a concentration effective to inhibit the polymerase or at a concentration effectivce to act as a substrate for the polymerase.

In still further contemplated aspects, nucleosides can be screened for their ability to inhibit HCV polymerase activity in vitro according to screening methods set forth more particularly herein. One can readily determine the spectrum of activity by evaluating the compound in the assays described herein or with another confirmatory assay.

In one especially preferred aspect, the efficacy of the anti-HCV compound is measured according to the concentration of compound necessary to reduce the virus replication in vivo, by 50% (i.e. the compound's $EC_{50}$) according to methods set forth more particularly herein. For example, the efficacy of an anti-HCV compound may be measured according to the concentration of compound necessary to reduce the virus replication in vivo, by 50% (i.e. the compound's $EC_{50}$) according to the method set forth more particularly herein. In particularly preferred aspects, the compound exhibits an $EC_{50}$ of less than 100, 50, 25, 15, 10, 5 or 1 micromolar.

Alternatively, nucleosides can be screened for their ability to inhibit HCV polymerase activity in vitro according to the screening methods set forth more particularly herein. One can readily determine the spectrum of activity by evaluating the compound in the assays described herein or with another confirmatory assay.

Synthesis of Contemplated Compounds

It should generally be recognized that nucleoside phosphonates according to the inventive subject matter may be synthesized using numerous protocols known to those skilled in the art. However, in a preferred procedure, synthesis of the nucleoside phosphonates may be achieved by condensing the phosphonate group to the modified nucleoside.

General synthesis of 5'-deoxy-5'-phosphonate nucleosides

Synthesis can be achieved by the modification of a preformed nucleoside as described in the general exemplary scheme below, and it should be specially pointed out that various sugar modifications may be introduced in the compounds according to the inventive subject matter using modified sugars before coupling of the sugar with the base, or by modifying the sugar portion in the nucleoside. Similarly, the heterocyclic base may be modified at any appropriate step in the synthesis of contemplated compounds.

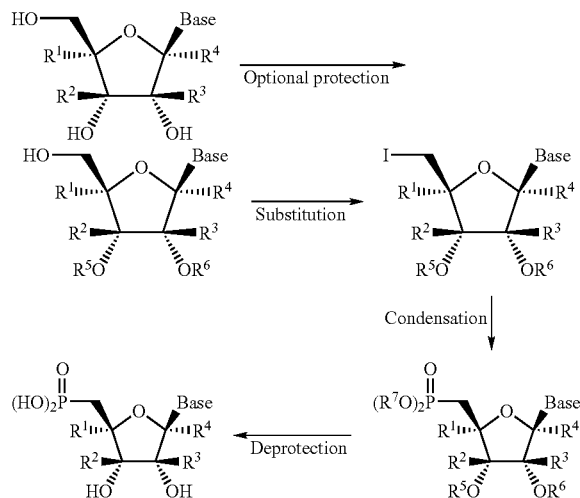

Figure 1A:
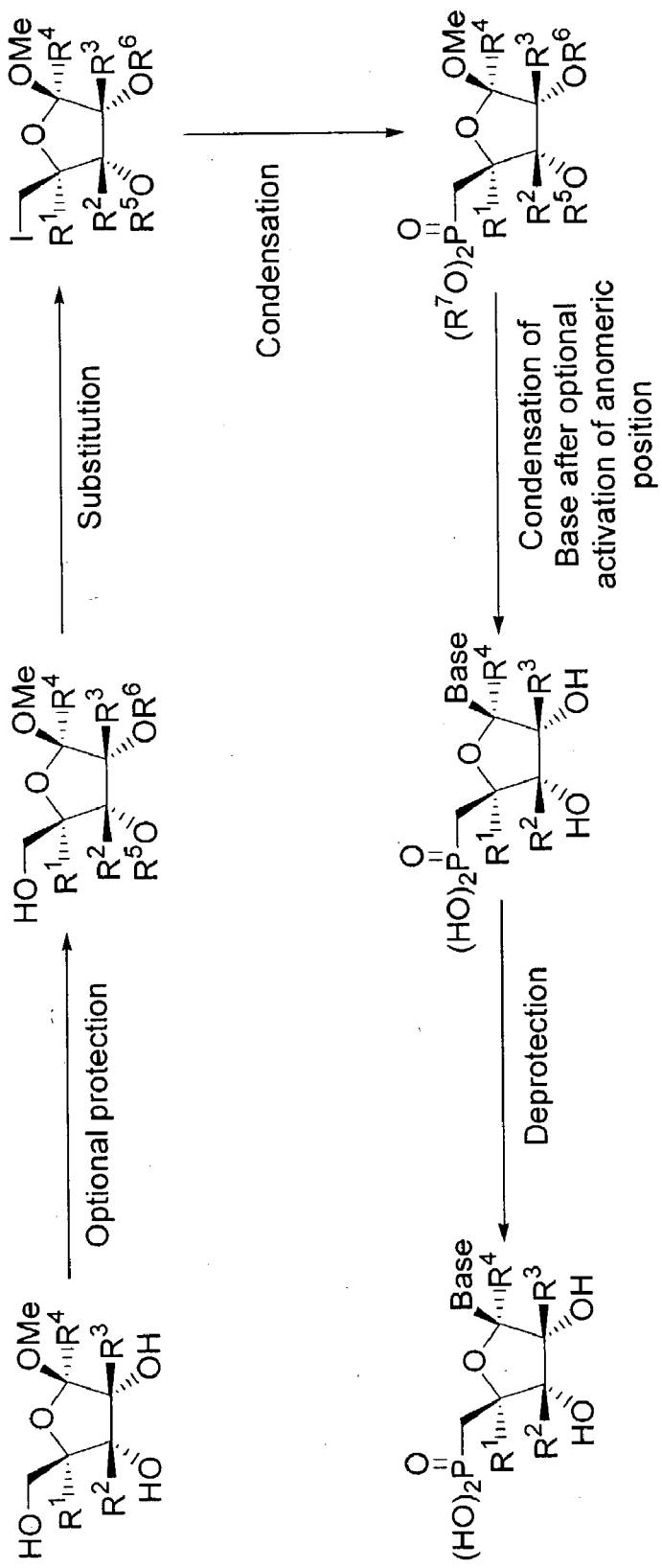
FIG. 1A depicts another contemplated route for the synthesis of exemplary 5'-deoxy-5'-phosphonate nucleosides.

In a particularly preferred aspect, the synthesis of a 5'-deoxy-5'-phosphonate nucleoside is achieved by the derivatization of the 5'-position of the preformed nucleoside as depicted in FIG. 1. A typical synthesis may be carried out by protecting 2'- and 3'-alcohols, and then converting the 5'-alcohol of the nucleoside into a 5'-bromo derivative by the reaction with carbon tetrabromide and triphenylphosphine. The Michaelis-Arbuzov reaction of the protected 5'-bromo nucleoside with triethyl phosphite yields the corresponding 5'-phosphonate nucleoside. Removal of the ethyl group by treatment with bromotrimethylsilane, followed by the deprotection of the benzoyl group provides the target compound. Alternatively, synthesis may also be achieved by modification of a sugar and condensation of the sugar phosphonate with the desired base as shown below in FIG. 1A.

Figure 2:
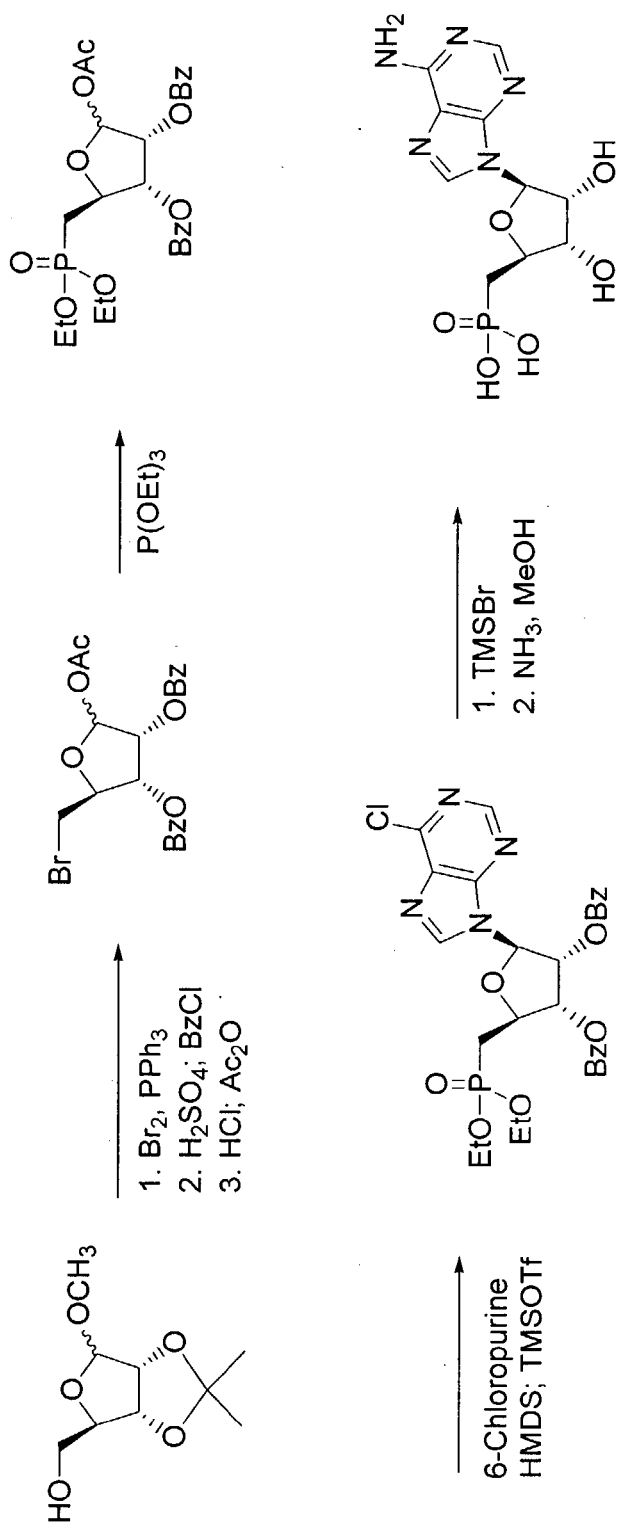
FIG. 2 depicts a further contemplated route for the synthesis of exemplary 5'-deoxy-5'-phosphonate nucleosides.

In a particular preferred aspect, synthesis of the 5'-deoxy-5'-phosphonate nucleoside is accomplished by the derivatization of the 5-position of sugar to make 5-phosphonate sugar and the subsequent glycosylation of the sugar phosphonate with various heterocyclic bases as depicted in FIG. 2. Here, methyl-2,3-O-isopropylidene-β-D-ribofuranose is readily converted to its 5-bromo derivative in high yield. After the activation of an anomeric position, the Michaelis-Arbuzov reaction is performed to yield the 5-phosphonate sugar derivative. 6-Chloropurine is silylated and then condensed with the 5-phosphonate sugar in the presence of trimethylsilyl triflate to afford the protected 5'-deoxy-5'-phosphonate nucleoside. Deprotection with bromotrimethylsilane provides the target compound.

General synthesis of 5'-deoxy-5'-methylphosphonate nucleosides

Figure 3:
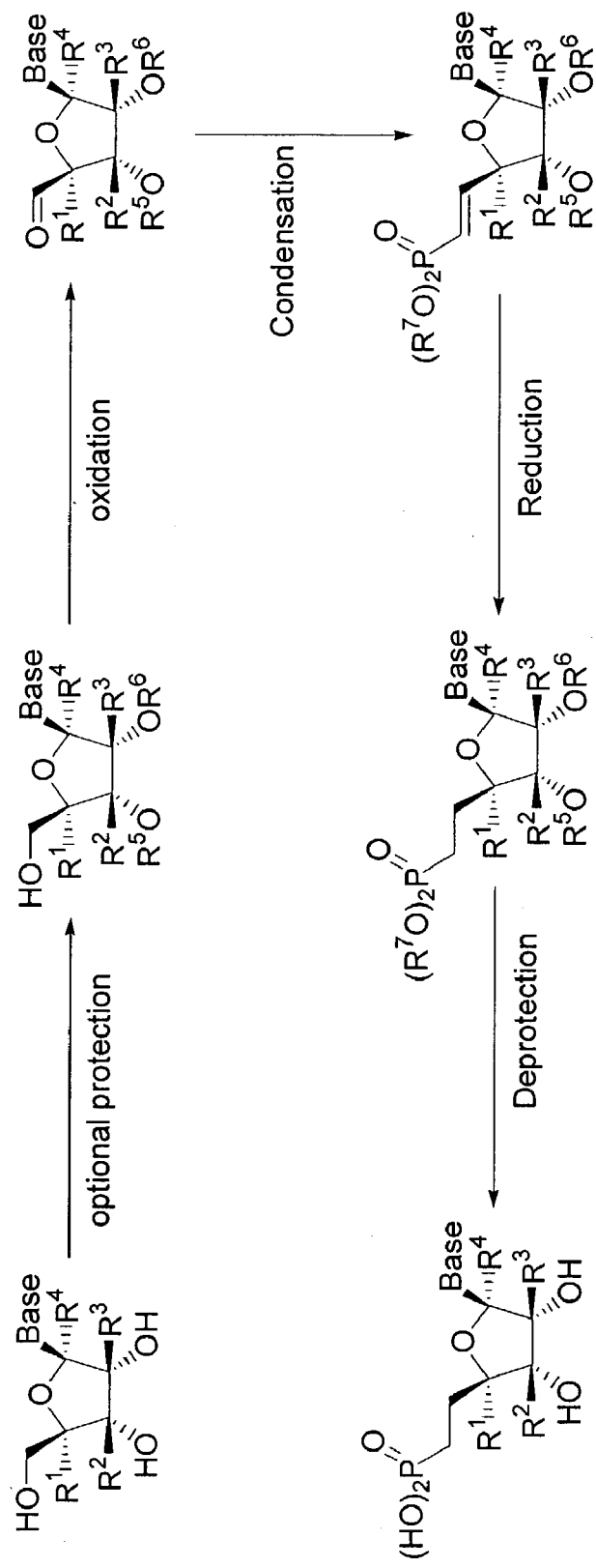
FIG. 3 depicts one contemplated route for the synthesis of exemplary 5'-deoxy-5'-methylenephosphonate nucleosides.
Figure 3A:
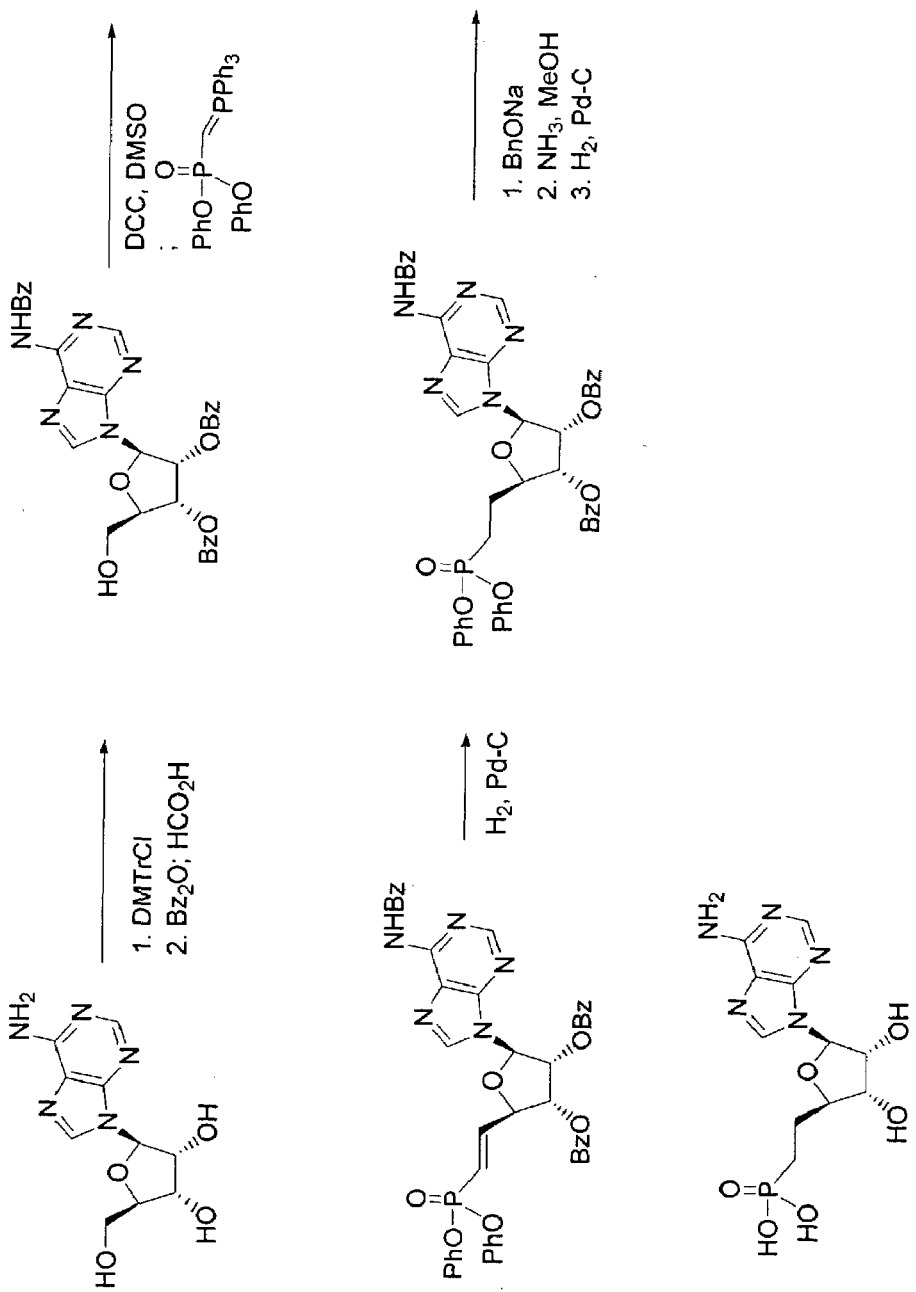
FIG. 3A depicts another contemplated route for the synthesis of exemplary 5'-deoxy-5'-methylenephosphonate nucleosides.

The synthesis of 5'-deoxy-5'-methylphosphonate nucleosides may be achieved by modification of a preformed nucleoside as described in exemplary FIG. 3. In a particularly contemplated embodiment, the synthesis of the 5'-deoxy-5'-methyl phosphonate nucleoside is accomplished by the reaction of the preformed nucleoside 5'-aldehyde with a stabilized Wittig reagent as depicted in FIG. 3A below. To modify the 5'-position of a nucleoside it is necessary to protect any reactive groups other than 5'-alcohol. Treatment of the protected nucleoside with dicyclohexylcarbodiimide and dimethyl sulfoxide in the presence of pyridium trifluoroacetate produces a 5'-aldehyde, which is treated with Wittig reagent, diphenyl triphenylphosphoranylidenemethylphosphonate, to make a vinyl phosphonate. Catalytic hydrogenation of the vinyl phosphonate with Pd—C gives a saturated phosphonate. Transesterification with sodium benzoxide, deprotection and palladium-catalyzed hydrogenolysis of benzyl ester provides the desired 5'-deoxy-5'-methyl phosphonate nucleoside.

Figure 3B:
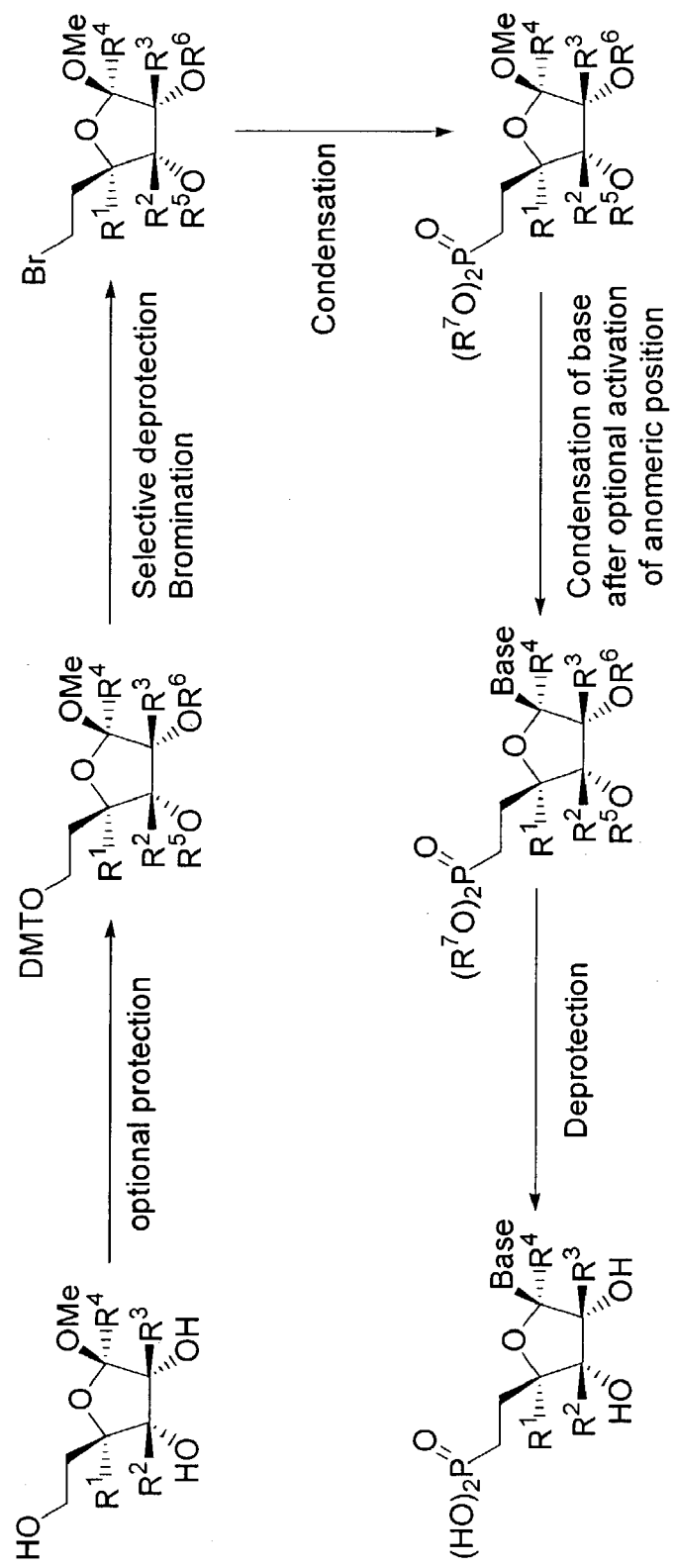
FIG. 3B depicts a further contemplated route for the synthesis of exemplary 5'-deoxy-5'-methylenephosphonate nucleosides.

Alternatively, the synthesis may also be achieved by modification of a sugar and condensation of the sugar phosphonate with the desired base as shown on the general example in FIG. 3B.

Figure 4:
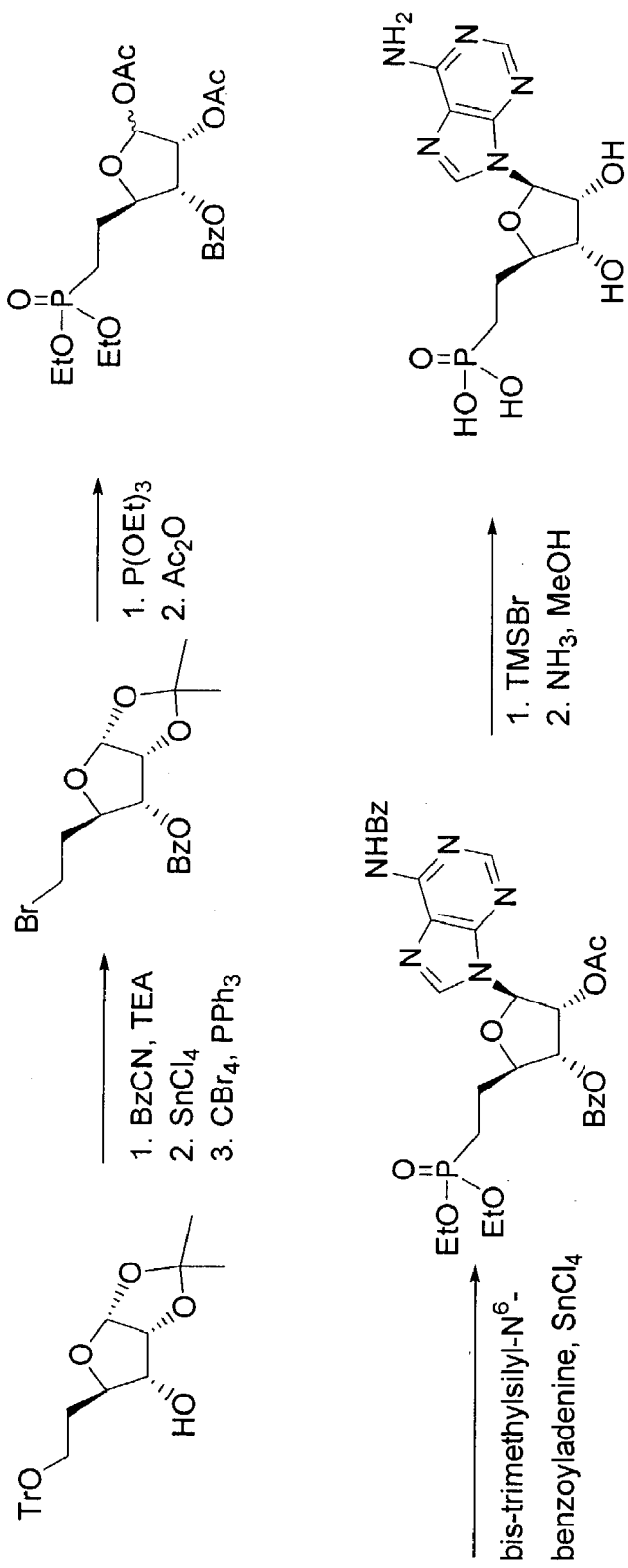
FIG. 4 depicts yet another contemplated route for the synthesis of exemplary 5'-deoxy-5'-methylenephosphonate nucleosides.
Figure 4A:
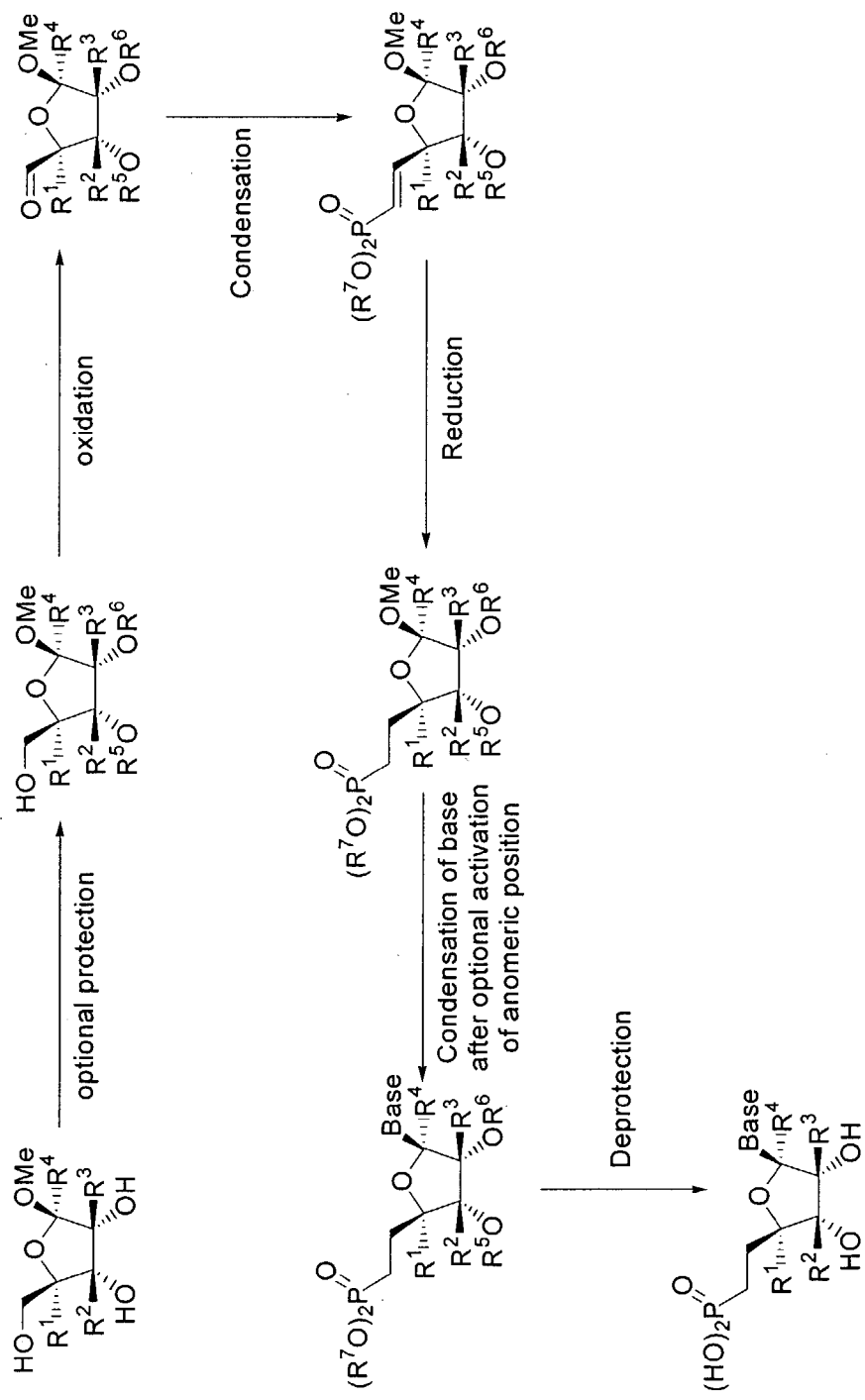
FIG. 4A depicts a still further contemplated route for the synthesis of exemplary 5'-deoxy-5'-methylenephosphonate nucleosides.

In a particularly preferred aspect, the 5'-deoxy-5'-methyl phosphonate nucleoside can be prepared starting from ribohexofuranose as shown in FIG. 4. Application of the similar strategy described in FIG. 2, i.e. bromination-Arbuzov reaction-glycosylation-deprotection sequence, affords the target nucleoside phosphonate. Alternatively, the sugar phosphonate can be prepared in a slightly different manner, as described in FIG. 4A.

Figure 5:
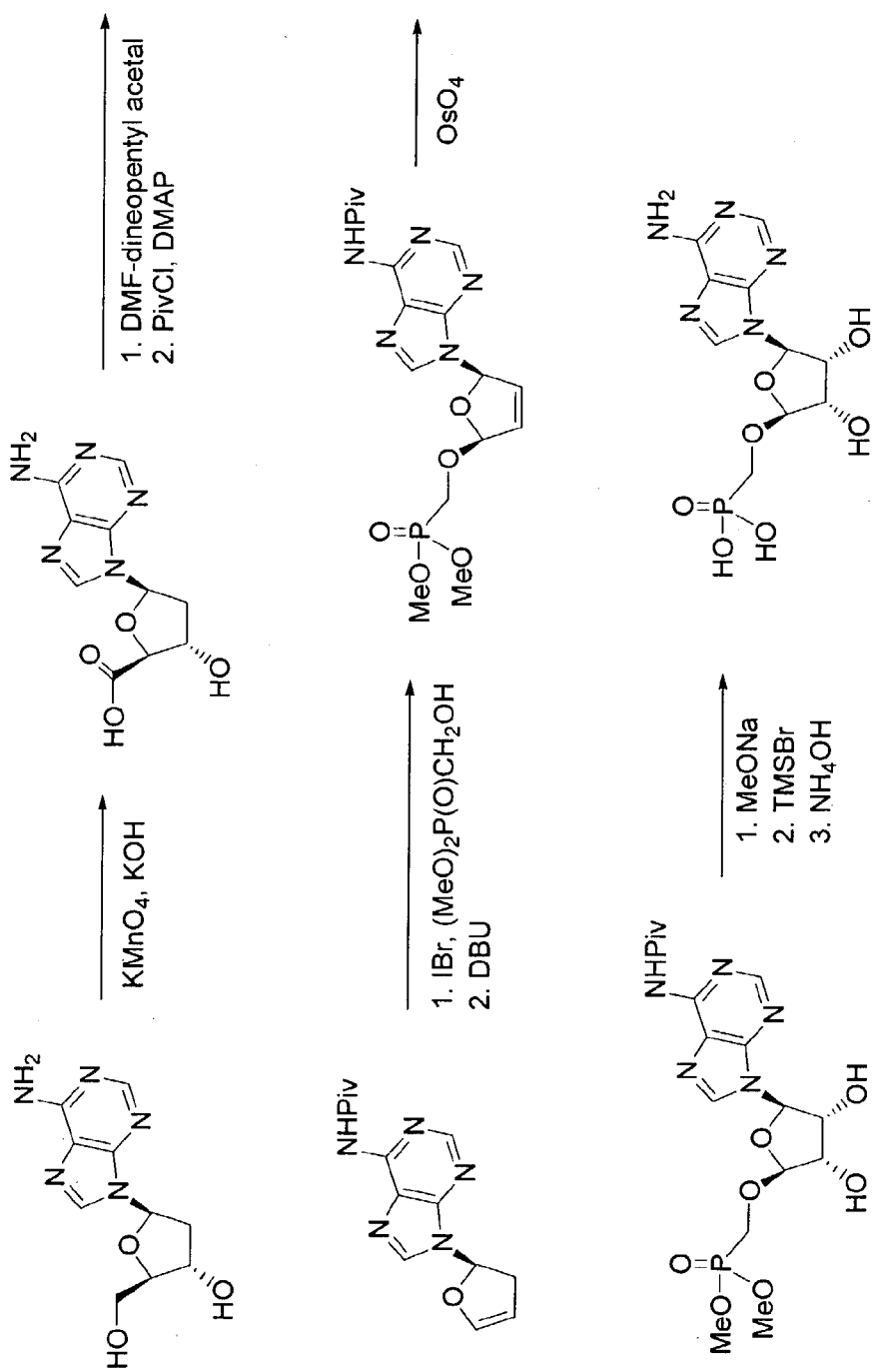
FIG. 5 depicts one contemplated route for the synthesis of exemplary 5'-phosphonate nucleotide analogs.

In yet another particularly preferred aspect, synthesis of a phosphonate isostere of a nucleoside monophosphate is achieved by using 2'-deoxyadenosine as a starting material as depicted in FIG. 5. A typical synthesis is carried out by oxidizing the 5'-hydroxyl group of 2'-deoxyadenosine with potassium permanganate to give the corresponding 5'-carboxylic acid. Decarboxylative elimination of the carboxylic acid provides furanoid glycal. Regio- and stereo-selective addition of dimethyl (hydoxymethyl)phosphonate to a double bond of the furanoid glycal is mediated by iodine monobromide. 1,8-diazabicyclo[5,5,0]undec-7-ene-catalyzed elimination of the resulting iodide intermediate provides 2,5-dihydrofuran derivative. Bis-hydroxylation on the double bond of the dihydrofuran with osmium tetraoxide and 4-methyl-morpholine-N-oxide, followed by removal of protecting groups provides the target compound.

Figure 6:
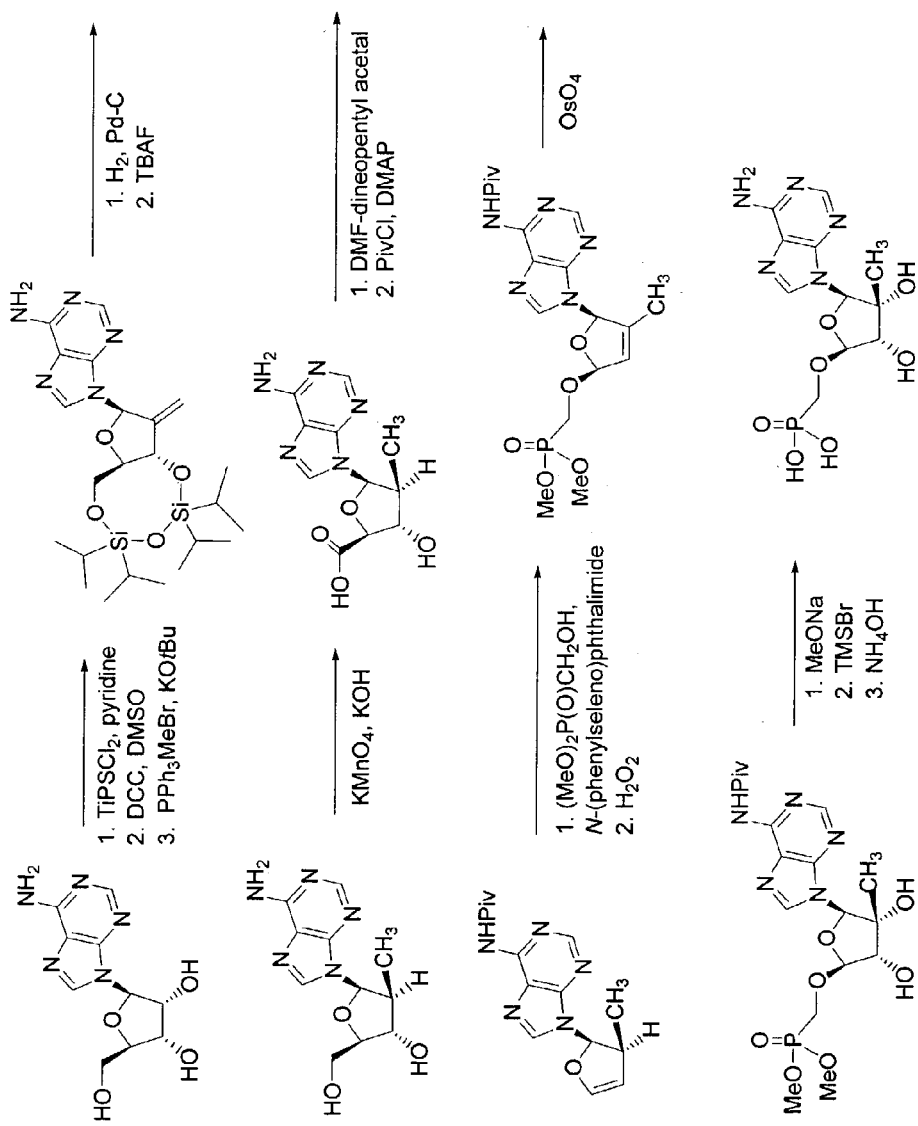
FIG. 6 depicts another contemplated route for the synthesis of exemplary sugar-modified 5'-phosphonate nucleotide analogs.

Alternatively, a similar synthetic strategy can be applied toward the synthesis of the phosphonate analogue containing methyl group at the 2' position of the sugar as shown in FIG. 6 below. Protection of 3'- and 5'-hydroxyl groups of adenosine by silylation, followed by oxidation of the 2'-hydroxyl with dicyclohexylcarbodiimide and dimethyl sulfoxide affords the ketone derivative. Wittig reaction of the ketone derivative with methyltriphenylphosphonium bromide provides the corresponding 2'-methylideneadenosine. Hydrogenation in the presence of Pd—C, followed by desilylation affords 2'-deoxy-2'-methyladenosine, can be converted into the desired phosphonate isostere by repeating the same sequence described in FIG. 5.

Figure 7:
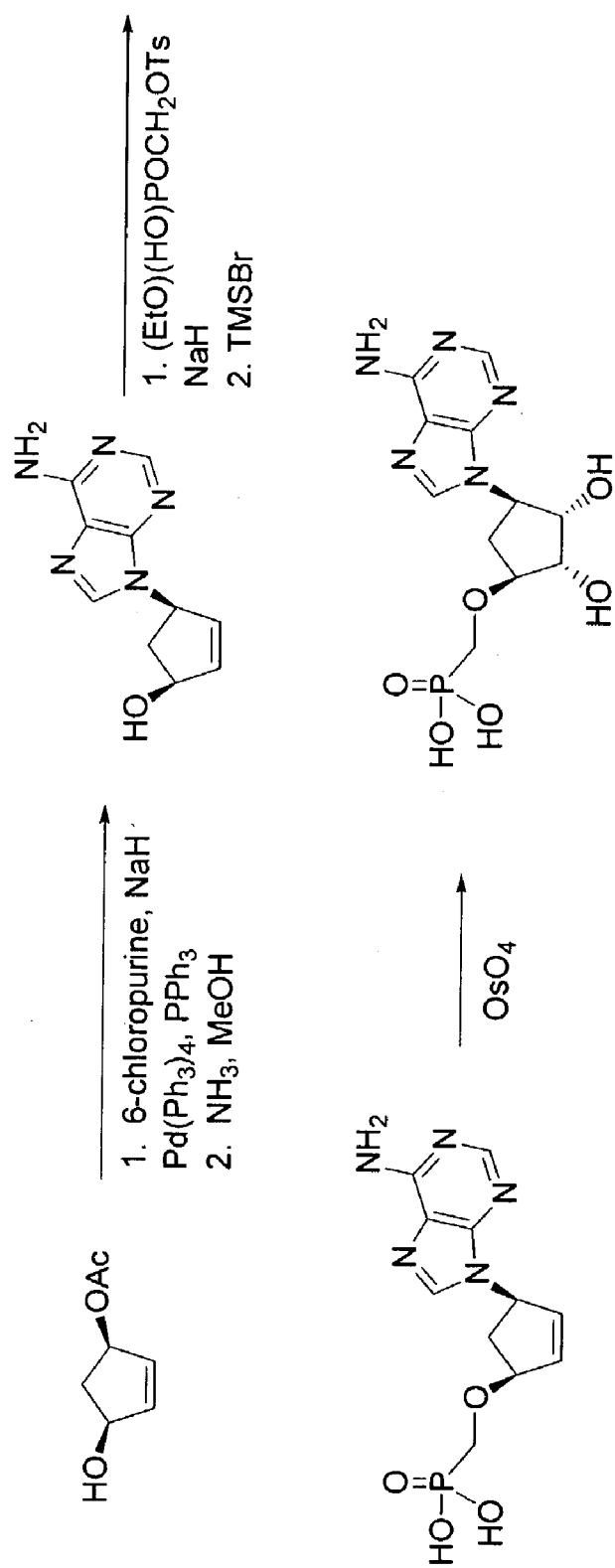
FIG. 7 depicts yet another contemplated route for the synthesis of exemplary 5'-phosphonate nucleotide analogs.

In a still further preferred aspect of the inventive subject matter, the synthesis of a carboxylic phosphonate is described as indicated in FIG. 7 below. Here, the carbocyclic nucleoside can be formed directly by palladium-catalyzed reaction of a sodium salt of 6-chloropurine with the enantiomerically pure allylic acetate. Subsequent amination of the 6-chloro nucleoside gives an adenine derivative. It is then treated with p-tolylsulfonyloxy-methanephosphonate in the presence of a base to provide the corresponding nucleoside phosphonate. Removal of the ethyl group by treatment of bromotrimethylsilane, followed by bis-hydroxylation with osmium tetraoxide affords the target compound.

EXAMPLES

9-[5'-deoxy-5'-(dihyoxyphosphinyl)-β-D-ribo-furanosyl]adenine (FIG. 2)

Methyl 2,3-di-O-benzoyl-5-bromo-5-deoxy-d-ribofuranoside: A solution of methyl (5-deoxy-5-bromo-2,3-O-isopropylidene-)-β-D-ribofuranose (100 g, 0.4 mol) in MeOH (600 mL) was treated with 0.05 N aqueous sulfuric acid (200 mL) and refluxed for 10 h. The solution was neutralized with saturated NaHCO$_3$ and the volatiles were removed under reduced pressure. The solution was extracted with EtOAc (10×100 mL) and the combined organic solution was washed with brine (500 mL), dried with Na$_2$SO$_4$, and concentrated to dryness. The resulting yellow oil was dissolved in pyridine (500 mL) and treated with benzoyl chloride (118 g, 0.84 mol) and the reaction was stirred at room temperature for 20 h. The mixture was diluted with slow addition of H$_2$O (500 mL) and extracted with ether (5×200 mL). The combined organic solution was washed with 3N ice-cold sulfuric acid (5×200 mL) and brine (2×200 mL), dried with Na$_2$SO$_4$, and concentrated to dryness. Silica gel chromatography (EtOAc:Hexanes=40:60) yielded 127 g of the target compound (75%).

2,3-Di-O-benzoyl-5-bromo-5-deoxyribofuranosyl acetate: The compound obtained in step a.) (127 g, 0.29 mol) in dioxane (1300 mL) was refluxed with 1 N HCl for 22 h. The solution was neutralized with saturated NaHCO$_3$ and the volatiles were removed under reduced pressure. The mixture was extracted with EtOAc (10×100 mL) and the combined organic solution was washed with brine (500 mL), dried with Na$_2$SO$_4$, and concentrated to dryness. The red syrup was dissolved in pyridine (200 mL) and treated with acetyl chloride (50 mL) and DMAP (1 g) and the reaction was stirred at room temperature for 20 h. The mixture was diluted with slow addition of H$_2$O (200 mL) and extracted with CH$_2$Cl$_2$ (5×200 mL). The combined organic solution was washed with 3N ice-cold sulfuric acid (5×100 mL) and brine (2×100 mL), dried with Na$_2$SO$_4$, and concentrated to dryness. Silica gel chromatography (EtOAc:Hexanes=40:60) yielded 68 g of the target compound (50%).

1-O-Acetyl-2,3-di-O-benzoyl-5-deoxy-5-(diethoxyphosphinyl)-D-ribofuranose: 2,3-Di-O-benzoyl-5-bromo-5-deoxyribofuranosyl acetate (68.0 g, 0.143 mol) was dissolved in triethyl phosphite (205 mL) and the solution was heated under reflux for 30 h. The volatiles were removed under reduced pressure and the resulting oil was dissolved in ether (780 mL). The organic solution was washed with brine (2×100 mL), dried with Na$_2$SO$_4$, and concentrated to dryness. Silica gel chromatography (EtOAc:Hexanes=80:20) yielded 59.4 g of the target compound (78%).

9-[5'-Deoxy-2',3'-O-benzoyl-5'-(diethoxyphosphinyl)-β-D-ribofuranosyl]-6-chloropurine: 6-Chloropurine (1.75 g, 10 mmol) was mixed with HMDS (50 mL) and refluxed with ammonium sulfate (0.1 g) for 4 h. The mixture was evaporated and dried in vacuo for 2 h. The solid was dissolved in CH$_3$CN (10 mL) and treated with the compound obtained in step c.) in CH$_3$CN (10 mL) followed by the additon of TMSOTf (6.67 g, 30 mmol). After 24 h at room temperature, the mixture was poured into saturated NaHCO$_3$. The mixture was extracted with EtOAc (10×25 mL) and the combined organic solution was washed with brine (100 mL), dried with Na$_2$SO$_4$, and concentrated to dryness. Silica gel chromatography (CH2Cl2:Acetone=80:20) yielded 3.69 g of the target compound (60%).

9-[5'-deoxy-5'-(dihyoxyphosphinyl)-β-D-ribo-furanosyl]adenine: The compound obtained in step d.) (3.07 g, 5 mmol) in CH$_3$CN (10 mL) was treated with bromotrimethylsilane (2.3 g, 15 mmol) and stirred for 6 h. The volatiles were removed under reduced pressure, and the crude was dissolved in methanolic ammonia (50 mL) and heated in a bomb at 80° C. for 16 h. The solution was concentrated to 10 mL and 10 mL of H$_2$O was added and extracted with CH$_2$Cl$_2$ (3×20 mL). The organic layer was washed with H$_2$O and the combined H$_2$O solution was chromatographed on the DEAE-cellulose column with ammonium bicarbonate. Concentration yielded 0.93 g of the target compound (51%).

9-[5',6'-dideoxy-6'-(hydroxyphosphinyl)-β-D-ribo-hexofuranosyl)adenine (FIG. 4)

9-(5'-O-(4,4'-dimethoxytrityl-β-D-ribofuranosyl)adenine: To a suspension of adenosine (1) (29.0 g, 113 mmol), which was dried in vacuo for 8 h at 80° C. with P$_2$O$_5$, in a mixture of DMF (900 mL) and pyridine (100 mL) was added 4,4'-dimethoxytrityl chloride (41.9 g, 121 mmol). The reaction mixture was stirred at room temperature for 2 days and quenched by the addition of H$_2$O (50 mL). After stirring for 1 h, the mixture was evaporated and the resulting slurry was poured into saturated NaHCO$_3$ solution (1.5 L). The white precipitate was collected by vacuum filtration and washed with cold H$_2$O (200 mL). The resulting solid was dried and recrystallized in ethyl acetate-benzene mixture to yield 27.3 g (44%) of 9-(5'-O-(4,4'-dimethoxytrityl-β-D-ribofuranosyl) adenine as a white solid.

N$^6$-Benzoyl-9-(2',3'-di-O-benzoyl-β-D-ribofuranosyl)adenine: To a solution of 9-(5'-O-(4,4'-dimethoxytrityl-β-D-ribofuranosyl)adenine (17.1 g, 30.2 mmol) in anhydrous pyridine (250 mL) was added benzoic anhydride (27.3 g, 120.8 mmol). The reaction mixture was heated under reflux for 3 h. The excess benzoic anhydride was quenched by the additon of MeOH (20 mL), followed by a 15 min reflux period. The mixture was concentrated to dryness and dissolved in CHCl$_3$ (500 mL). The organic solution was washed with saturated NaHCO$_3$ (2×300 mL) and brine (1×300 mL), dried with Na$_2$SO$_4$, and concentrated to dryness. The crude benzoylated product was treated with a 2;2;1 mixture of H$_2$O-formic acid-THF (500 mL). The solution was stirred at room temperature for 1 h and neutralized with the addition of 50% aqueous NaOH solution. The solution was extracted with CHCl$_3$ (3×200 mL) and the combined organic solution was washed with brine (1×100 mL), dried with Na$_2$SO$_4$, and concentrated to dryness. Recrystallization in ethanol yielded 8.2 g (82%) of the target compound as a white solid.

N$^6$-Benzoyl-9-[2',3'-di-O-benzoyl-5',6'-dideoxy-6'-(diphenoxyphosphinyl)-β-D-ribo-hex-5-enofuranosyl]adenine: To a solution of the compound obtained in step b.) (1.65 g, 2.84 mmol), 1,3-dicyclohexylcarbodiimide (2.34 g, 11.4 mmol) and pyridine (0.32 mL) in anhydrous DMSO (15 mL) was added trifluoroacetic acid (0.15 mL) and the mixture was stirred at room temperature for 22 h. To the mixture was added diphenyl (triphosphoranylidene)methylphosphonate (2.89 g, 5.68 mmol) and stirring was continued for 24 h. Excess carbodiimide was hydrolyzed by a careful addition of a solution of oxalic acid dihydrate (771 mg, 8.56 mmol) in MeOH (3 mL). After stirring for 10 min, the volatiles were removed under reduced pressure and the urea formed was removed by vacuum filtration. The filtrate was extracted with EtOAc (300 mL) and the organic solution was washed with brine (2×100 mL), dried with Na$_2$SO$_4$, and concentrated to dryness. Silica gel chromatography (EtOAc) yielded 1.43 g of the target compound (62%).

N$^6$-Benzoyl-9-[2',3'-di-O-benzoyl-5',6'-dideoxy-6'-(diphenoxyphosphinyl)-β-D-ribo-hexofuranosyl]adenine: To a solution of the vinylphosphonate (800 mg, 0.99 mmol) in MeOH (30 mL) was added Pd—C (10%, 300 mg) and the reaction mixture was stirred under 30 psi of hydrogen. After 20 h, the mixture was filtered through Celite to remove the catalyst and the filtrate was evaporated to dryness. Silica gel chromatography (EtOAc:Hexanes=75:25) yielded 410 mg of the target compound (51%).

$N^6$-benzoyl-9-[5',6'-dideoxy-6'-(dibenzyloxyphosphinyl)-β-D-ribo-hexofuranosyl]adenine: Sodium hydride (100 mg, 2.5 mmol) was added to 5 mL of benzyl alcohol and the resulting suspension was stirred for 30 min. To the mixture was added a solution of the compound obtained in step d.) (360 mg, 0.44 mmol) in anhydrous DMSO (5 mL). The reaction was stirred at room temperature for 4 h and quenched with saturated $NH_4Cl$ solution (20 mL). The mixture was extracted with EtOAc (2×30 mL) and the combined organic solution was washed with brine (30 mL), dried with $Na_2SO_4$, and concentrated to dryness. Silica gel chromatography (EtOAc:MeOH=90:10) yielded 190 mg of $N^6$-benzoyl-9-[5',6'-dideoxy-6'-(dibenzyloxyphosphinyl)-β-D-ribo-hexofuranosyl]adenine (69%).

9-[5',6'-dideoxy-6'-(dibenzyloxyphosphinyl)-β-D-ribo-hexofuranosyl]adenine: A solution of the compound obtained in step e.) (190 mg, 0.30 mmol) in methanolic ammonia (40 mL, saturated at 0° C.) was stirred at room temperature in a sealed bomb for 24 h. The bomb was cooled to 0° C. before opening. The reaction mixture was stirred at RT for 1 h and then concentrated to dryness. Silica gel chromatography ($CH_2Cl_2$:MeOH=90:10) yielded 146 mg of the target compound (92%) as a pale foam.

9-[5',6'-dideoxy-6'-(hydroxyphosphinyl)-β-D-ribo-hexofuranosyl]adenine: To a solution of the compound obtained in step d.) (146 mg, 0.28 mmol) in MeOH (20 mL) was added Pd—C (10%, 150 mg) and the reaction mixture was stirred under hydrogen at atmospheric pressure. After 16 h, the mixture was filtered through Celite to remove the catalyst and the filtrate was evaporated to dryness. The resulting solid obtained was washed with $CH_2Cl_2$ (1 mL) to yield 53 mg of the target compound (55%) as a white solid.

(2R, 3R, 4S, 5R)-9-[Tetrahydro-3,4-dihydroxy-5-(phosphonomethoxy)-2-furanyl]adenine (FIG. 5)

2'-Deoxyadenosine-5'-carboxylic acid: To a solution of 2'-deoxyadenosine (8.60 g, 32 mol) in $H_2O$ (1 L) was added dropwise solutions of $KMnO_4$ (15.0 g, 95 mmol) ) in $H_2O$ (1 L) and KOH (4.0 g, 71 mmol) ) in $H_2O$ (500 mL). The reaction mixture was stirred at room temperature for 3 days and an excess $KMnO_4$ was quenched with a slow addition of 30% $H_2O_2$. The mixture was filtered under reduced pressure and the filtrate was concentrated to 200 mL and the resulting solution was acidified to pH 4.5 with 3N HCl. The precipitate was filtered and dried in vacuo at 40° C. for 8 h to yield 2.53 g of the target compound (30%) as a white solid.

9-[2,3-Dihydro-2(R)-furanyl-$N^6$-pivaloyladenine: To a suspension of the compound obtained in step a.) (2.53 g, 8.9 mol) in DMF (100 mL) was added N,N-dimethylformamide dineopentyl acetal (7.6 mL, 29 mmol). The reaction mixture was stirred at 95° C. for 16 h and concentrated to dryness. The residue was dissolved in a mixture of MeOH (65 mL) and concentrated $NH_4OH$ (65 mL) and stirred at room temperature for 24 h. The volatiles were removed under reduced pressure. Silica gel chromatography ($CH_2Cl_2$:MeOH=90:10) yielded 1.31 g of 9-[2,3-dihydro-2(R)-furanyladenine (61%) as a white solid. To a solution of the compound obtained above (1.70 g, 8.4 mol), pyridine (0.82 mL, 10.2 mmol) and 4-dimethylaminopyridine (145 mg, 1.2 mmol) in 1,2-dichloroethane (60 mL) was added pivaloyl chloride (1.22 mL, 9.9 mmol). The reaction mixture was stirred at 65° C. for 16 h and diluted with $CH_2Cl_2$ (300 mL). The organic solution was washed with brine (500 mL), dried with $Na_2SO_4$, and concentrated to dryness. Silica gel chromatography ($CH_2Cl_2$:MeOH=97:3) yielded 1.30 g of the target compound (51%).

(2R, 5R)-$N^6$-Pivaloyl-9-[2,5-Dihydro-5-[(dimethoxyphosphinyl)methoxy]-2-furanyl]adenine: To a solution of the compound obtained in the previous step (980 mg, 3.4 mol) and dimethyl(hydroxymethyl)phosphonate (1.71 g, 13.6 mmol) in $CH_2Cl_2$ (8 mL) at −25° C. was added dropwise a solution of iodine monobromide (1.41 g, 6.8 mmol) ) in $CH_2Cl_2$ (8 mL). The reaction mixture was stirred at −25° C. for 8 h and diluted with $CH_2Cl_2$ (100 mL). The organic solution was washed with aqueous $NaHCO_3$ (50 mL), aqueous sodium bisulfite (2×50 mL) and brine (500 mL), dried with $Na_2SO_4$, and concentrated to dryness. Silica gel chromatography ($CH_2Cl_2$:MeOH=95:5) yielded 1.70 g of (2R, 4S, 5R)-$N^6$-pivaloyl-9-[tetrahydro-4-iodo-5-[(dimethoxyphosphinyl)methoxy]-2-furanyl]adenine (90%). To a solution of the compound obtained above (811 mg, 1.5 mmol) THF (10 mL) was added 1,8-diazabicyclo[5,5,0]undec-7-ene (0.44 mL, 2.9 mmol). The reaction mixture was stirred at 60° C. for 5 h and the volatiles were removed under reduced pressure. The residue was dissolved in $CH_2Cl_2$ (300 mL) and the organic solution was washed with brine (200 mL), dried with $Na_2SO_4$, and concentrated to dryness. Silica gel chromatography ($CH_2Cl_2$:MeOH=95:5) yielded 381 mg of the target compound (61%).

(2R, 3R, 4S, 5R)-$N^6$-Pivaloyl-9-[tetrahydro-3,4-dihydroxy-5-[(dimethoxyphosphinyl)methoxy]-2-furanyl]adenine: To a solution of the compound obtained in the previous step (178 mg, 0.42 mol) and 4-methylmorpholine N-oxide (0.11 g, 0.63 mmol) in acetone (6 mL) and t-BuOH (1 mL) $OsO_4$ (0.26 ml, 0.020 mmol) was added. The reaction mixture was stirred at room temperature for 16 h and the volatiles were removed under reduced pressure. The residue was dissolved in EtOAc (100 mL) and the organic solution was washed with aqueous sodium thiosulfate (2×50 mL) and brine (50 mL), dried with $Na_2SO_4$, and concentrated to dryness. Silica gel chromatography ($CH_2Cl_2$:MeOH=90:10) yielded 145 mg of the target compound (75%).

(2R, 3R, 4S, 5R)-9-[Tetrahydro-3,4-dihydroxy-5-(phosphonomethoxy)-2-furanyl]adenine: To the compound obtained in the previous step (1.10 g, 2.8 mmol) in MeOH (15 mL) at 0° C. was added 25% sodium methoxide in MeOH (2.5 mL). The reaction mixture was stirred at room temperature for 7 h and neutralized to pH 8.0 by addition of 2 N HCl. The volatiles were removed under reduced pressure. The crude mixture was dissolved in DMF (15 mL) and treated with bromotrimethylsilane (3.5 mL) at 0° C. After stirring at room temperature for 6 h, the volatiles were removed in vacuo. The oil was diluted with concentrated $NH_4OH$ (1.5 mL) and reevaporated. $C_{18}$ reverse-phase chromatography with water yielded 0.55 g of the target compound (65%).

(2R, 3R, 4S, 5R)-9-[Tetrahydro-3,4-dihydroxy-3-methyl-5-(phosphonomethoxy)-2-furanyl]adenine (FIG. 6)

3',5'-O-(Tetraisopropyldisilyloxane-1,3-diyl)-2'-deoxy-2'-methylideneadenosine: To a suspension of adenosine (10.8 g, 40 mmol) in pyridine (1000 mL) at 0° C. was added 1,3-dichloro-1,1,3,3-tetraisopropyldisiloxane (15.5 mL, 48 mmol). The reaction mixture was stirred at room temperature for 2 days and quenched by an addition of ethanol (5 mL). The mixture was evaporated and the resulting oil was diluted with EtOAc (1000 mL). The organic solution was washed with aqueous $NaHCO_3$ (2×500 mL) and brine (500 mL), dried with $Na_2SO_4$, and concentrated to dryness. Silica gel chromatography ($CH_2Cl_2$:MeOH=90:10) yielded 18 g of 3',5'-O-(1,1,3,3,-tetraisopropyl-disiloxane-1,3-diyl)-adenosine (88%).

To a solution of the compound obtained above (2.5 g, 5.0 mmol), 1,3-dicyclohexylcarbodiimide (1.81 g, 8.8 mmol) and pyridine (0.48 mL) in anhydrous DMSO (15 mL) was added trifluoroacetic acid (0.23 mL). The mixture was stirred at room temperature for 22 h and excess carbodiimide was hydrolyzed by a careful addition of a solution of oxalic acid dihydrate in MeOH. After stirring for 10 min, the volatiles were removed under reduced pressure and the urea formed was removed by vacuum filtration. The filtrate was extracted with EtOAc (300 mL) and the organic solution was washed with brine (2×100 mL), dried with $Na_2SO_4$, and concentrated to dryness. The resulting crude was dissolved in benzene (15 mL) and the solution was cooled down to −78° C. The mixture was added to a solution of $PPh_3MeBr$ (3.57 g, 10 mmol) and sodium pentoxide (0.99 g, 9 mmol) in ether (125 mL), which was pre-stirred at room temperature for 2 h. After the addition, the reaction mixture was slowly warmed to 4° C. at which temperature the mixture was kept for 48 h. The reaction mixture was washed with brine (2×100 mL), dried with $Na_2SO_4$, and concentrated to dryness. Silica gel chromatography ($CH_2Cl_2$) yielded 1.52 g of the target compound (60%).

2'-Deoxy-2'-methyladenosine: To a solution of the compound obtained in the previous step (320 mg, 1.1 mmol) in MeOH (44 mL) was added Pd—C (10%, 200 mg) and the reaction mixture was stirred under 5 psi of hydrogen. After 4 h, the mixture was filtered through Celite to remove the catalyst and the filtrate was evaporated to dryness. Silica gel chromatography ($CH_2Cl_2$:MeOH=90:10) yielded 240 mg of the reduced compound (75%). To a solution of the reduced compound (240 mg, 0.82 mmol) in THF (20 mL) was added 1 M solution of TBAF (2.5 mL, 2.5 mmol) in THF. The reaction mixture was stirred at room temperature for 1 h and the volatiles were removed under reduced pressure. Silica gel chromatography ($CH_2Cl_2$:MeOH=80:20) yielded 196 mg of the target compound (90%).

2'-Deoxy-2'-methyladenosine-5'-carboxylic acid: To a solution of the compound obtained in the previous step (8.60 g, 32 mol) in $H_2O$ (1 L) was added dropwise solutions of $KMnO_4$ (15.0 g, 95 mmol) ) in $H_2O$ (1 L) and KOH (4.0 g, 71 mmol) ) in $H_2O$ (500 mL). The reaction mixture was stirred at room temperature for 3 days and excess $KMnO_4$ was quenched with a slow addition of 30% $H_2O_2$. The mixture was filtered under reduced pressure and the filtrate was concentrated to 200 mL and the resulting solution was acidified to pH 4.5 with 3N HCl. The precipitate was filtered and dried in vacuo at 40° C. for 8 h to yield.2.53 g of the target compound (30%) as a white solid.

9-[2,3-Dihydro-3-methyl-2(R)-furanyl-$N^6$-pivaloyladenine: To a suspension of the compound obtained in the previous step (2.53 g, 8.9 mol) in DMF (100 mL) was added N,N-dimethylformamide dineopentyl acetal (7.6 mL, 29 mmol). The reaction mixture was stirred at 95° C. for 16 h and concentrated to dryness. The residue was dissolved in a mixture of MeOH (65 mL) and concentrated $NH_4OH$ (65 mL) and stirred at room temperature for 24 h. The volatiles were removed under reduced pressure. Silica gel chromatography ($CH_2Cl_2$:MeOH=90:10) yielded 1.31 g of 9-[2,3-dihydro-3-methyl-2(R)-furanyladenine (61%) as a white solid. To a solution of the compound obtained above (1.70 g, 8.4 mol), pyridine (0.82 mL, 10.2 mmol) and 4-dimethylaminopyridine (145 mg, 1.2 mmol) in 1,2-dichloroethane (60 mL) was added pivaloyl chloride (1.22 mL, 9.9 mmol).

The reaction mixture was stirred at 65° C. for 16 h and diluted with $CH_2Cl_2$ (300 mL). The organic solution was washed with brine (500 mL), dried with $Na_2SO_4$, and concentrated to dryness. Silica gel chromatography ($CH_2Cl_2$:MeOH=97:3) yielded 1.30 g of the target compound (51%).

(2R, 5R)-$N^6$-Pivaloyl-9-[2,5-Dihydro-5-[(dimethoxyphosphinyl)methoxy]-3-methyl-2-furanyl]adenine: To a solution of the compound obtained in the previous step (980 mg, 3.4 mol) and dimethyl(hydroxymethyl)phosphonate (1.71 g, 13.6 mmol) in $CH_2Cl_2$ (8 mL) at −25° C. was added dropwise a solution of IBr (1.41 g, 6.8 mmol) ) in $CH_2Cl_2$ (8 mL). The reaction mixture was stirred at −25° C. for 8 h and diluted with $CH_2Cl_2$ (100 mL). The organic solution was washed with, aqueous $NaHCO_3$ (50 mL), aqueous sodium bisulfite (2×50 mL) and brine (500 mL), dried with $Na_2SO_4$, and concentrated to dryness. Silica gel chromatography ($CH_2Cl_2$:MeOH=95:5) yielded 1.70 g of (2R, 4S, 5R)-$N^6$-pivaloyl-9-[tetrahydro-4-iodo-5-[(dimethoxyphosphinyl)methoxy]-3-methyl-2-furanyl]adenine (90%).

To a solution of the compound obtained above (811 mg, 1.5 mmol) in THF (10 mL) was added 1,8-diazabicyclo[5,5,0]undec-7-ene (0.44 mL, 2.9 mmol). The reaction mixture was stirred at 60° C. for 5 h and the volatiles were removed under reduced pressure. The residue was dissolved in $CH_2Cl_2$ (300 mL) and the organic solution was washed with brine (200 mL), dried with $Na_2SO_4$, and concentrated to dryness. Silica gel chromatography ($CH_2Cl_2$:MeOH=95:5) yielded 381 mg of the target compound (61%).

(2R, 3R, 4S, 5R)-$N^6$-Pivaloyl-9-[tetrahydro-3,4-dihydroxy-5-[(dimethoxyphosphinyl)methoxy]-3-methyl-2-furanyl]adenine: To a solution of the compound obtained in the previous step (178 mg, 0.42 mol) and 4-methylmorpholine N-oxide (0.11 g, 0.63 mmol) in acetone (6 mL) and t-BuOH (1 mL) was added $OsO_4$ (0.26 ml, 0.020 mmol). The reaction mixture was stirred at room temperature for 16 h and the volatiles were removed under reduced pressure. The residue was dissolved in EtOAc (100 mL) and the organic solution was washed with aqueous sodium thiosulfate (2×50 mL) and brine (50 mL), dried with $Na_2SO_4$, and concentrated to dryness. Silica gel chromatography ($CH_2Cl_2$:MeOH=90:10) yielded 145 mg of the target compound (75%).

(2R, 3R, 4S, 5R)-9-[Tetrahydro-3,4-dihydroxy-3-methyl-5-(phosphonomethoxy)-2-furanyl]adenine: To the compound obtained in the previous step (1.10 g, 2.8 mmol) in MeOH (15 mL) at 0° C. was added 25% sodium methoxide in MeOH (2.5 mL). The reaction mixture was stirred at room temperature for 7 h and neutralized to pH 8.0 by an addition of 2 N HCl. The volatiles were removed under reduced pressure. The crude was dissolved in DMF (15 mL) and was treated with bromotrimethylsilane (3.5 mL) at 0° C. After stirring at room temperature for 6 h, the volatiles were removed in vacuo. The oil was diluted with concentrated $NH_4OH$ (1.5 mL) and reevaporated. $C_{18}$ reverse-phase chromatography with water yielded 0.55 g of the target compound (65%).

(1R, 2R, 3S, 4S)-9-[2,3-Dihydroxy-4-(phosphonomethoxy)-cyclopent-1-yl]adenine (FIG. 7)

(1R, 4S)-9-(4-Hydroxycyclopent-2-en-1-yl)-9H-adenine: A suspension of 6-chloropurine (1.55 g, 10 mmol) and NaH (288 mg, 12 mmol) in THF (20 mL) was stirred at room temperature for 1.5 h. To the mixture was added a solution of (1R, 3S)-(+)-cyclopentene-1,3-diol 1-acetate (1.42 g, 10 mmol), Pd $(PPh_3)_4$ (1.15 g, 1.0 mmol) and $PPh_3$ (787 mg, 3.0 mmol) in THF (10 mL), and the reaction mixture was stirred at 70° C. for 18 h. The mixture was filtered through Celite and the volatiles were removed under reduced pressure. A solution of the crude material in methanolic ammonia (100 mL, saturated at 0° C.) was stirred at 100° C. in a sealed bomb for 3 h. The bomb was cooled to 0° C. before opening. The reaction mixture was stirred at room temperature for 1 h and then concentrated to dryness. Silica gel chromatography ($CH_2Cl_2$:MeOH=90:10) yielded 869 mg of the target compound (40%) as a pale foam.

(1R, 4S)-9-[4-(Phosphonomethoxy)-cyclopent-2-en-1-yl] adenine: To a solution of the compound obtained in the previous step (543 mg, 2.5 mmol) and NaH (150 mg, 3.8 mmol) in DMF (50 mL) was added a solution of (EtO)(HO)POCH$_2$OTs (735 mg, 2.5 mmol) in DMF. After 16 h, the mixture was neutralized with AcOH and the volatiles were removed under reduced pressure. The crude mixture was dissolved in DMF (15 mL) and treated with bromotrimethylsilane (3.5 mL) at 0° C. The reaction mixture was stirred at room temperature for 6 h and the volatiles were removed under reduced pressure. The oil was diluted with concentrated $NH_4OH$ (1.5 mL) and reevaporated. $C_{18}$ reverse-phase chromatography with water yielded 156 mg of the target compound (20%).

(1R, 2R, 3S, 4S)-9-[2,3-Dihydroxy-4-(phosphonomethoxy)-cyclopent-1-yl]adenine: To a solution of the compound obtained in the previous step (70 mg, 0.23 mol) and 4-methylmorpholine N-oxide (0.11 g, 0.63 mmol) in acetone (6 mL) and t-BuOH (1 mL) was added $OsO_4$ (0.26 ml, 0.020 mmol). The reaction mixture was stirred at room temperature for 16 h and the volatiles were removed under reduced pressure. $C_{18}$ reverse-phase chromatography with water yielded 32 mg of the target compound (40%).

Biological Data

Figure 8:
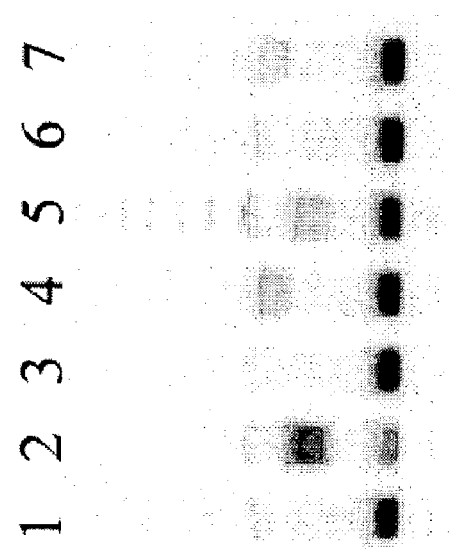
FIG. 8 is a phosphorimager scan of a polyacrylamide gel, showing incorporation of ATP and phosphonate analogues of ATP into RNA products by the NS5B RNA-dependent RNA polymerase of HCV.

Among other nucleotide analogs (data not shown), two exemplary phosphonate analogs of ATP, 5'-deoxy-5'-phosphonate (5'd-ATP) and 5'-deoxy-5'-methylene phosphonate (5'd-CH$_2$-ATP), were tested for inhibition and/or incorporation into an RNA product by the HCV RNA dependent RNA polymerase (RdRp). The incorporation reactions included 1 mM of the phosphonate analog or ATP, 10 μM of [$^{33}$P]GpC, 10 μM of 5'-AAAAAAAUGC-3', and 2.5 μM of HCV RdRp in a buffer that contained 50 mM Hepes, pH 7.3, 10 mM DTT, and 5 mM MgCl$_2$. The RNA products were resolved on a 25% polyacrylamide-7M urea-TBE gel. As shown in FIG. 8, extension of [$^{33}$P]GpC by HCV RdRp was observed with ATP or 5'd-CH$_2$-ATP, but no extension with 5'd-ATP. The incorporation of 5'd-CH$_2$-ATP is less efficient than that of ATP by 10-fold. To look for further elongation after incorporation of ATP or 5'd-CH$_2$-ATP, the same experiment was performed in the presence of additional UTP (1 mM). Elongation products by UTP were seen after ATP or 5'd-CH$_2$-ATP incorporation although those from the latter were much weaker in intensity. This result clearly demonstrates that HCV NS5B can incorporate a phosphonate nucleotide when it is isosteric to the natural substrate.

It should be especially recognized that there have been very few examples of utilizing phosphonates by either DNA or RNA polymerases. A phosphonate analog of AZT was shown to be very ineffective to HIV reverse transcriptase as both $K_m$ and $k_{cat}$ for incorporation are unfavorable by 3 orders of magnitude compared to those of AZT (Freeman, G. A. et al. *J. Med. Chem.* 1992, 35, 3192-3196). Phosphonate (5-deoxy) UTP was reported to be a pseudoterminator of RNA synthesis by *E. coli* RNA polymerase [Savochkina, L. P. et al. *Mol. Biol.* (*Mosk*) 1989, 23, 1700-1710]. However, to the best of the inventor's knowledge, no study has yet been reported for successful phosphonates as potential substrates or inhibitors for the HCV RNA-dependent RNA polymerase. Our study clearly demonstrated, for the first time, that a phosphonate analog of ATP may be utilized as a substrate by HCV RdRp. Interestingly, only that which is isosteric to ATP was incorporated by HCV RdRp to a lesser degree than ATP, indicating that the polymerase requires specific alignment between the α-phosphate of the elongation nucleotide and the 3'-OH of the preceding nucleotide for efficient phosphodiester bond formation.

Exemplary results of such tests are depicted in the autoradiograph of FIG. 8 showing RNA products from incorporations of ATP and phosphonate analogs of ATP by HCV RdRp. Each reaction contained 2.5 μM of RdRp, 10 μM of [$^{33}$P]GpC, 10 μM template, and the following nucleotides (1 mM): lane 1, none; lane 2, ATP; lane 3,5'-deoxy-5'-phosphonate ATP; lane 4,5'-deoxy-5'-methylene phosphonate ATP; lane 5, ATP and UTP; lane 6,5'-deoxy-5'-phosphonate ATP and UTP; lane 7,5'-deoxy-5'-methylene phosphonate ATP and UTP. The reaction products were resolved on a 25% polyacrylamide-7 M urea-TBE gel and the gel was scanned on a PhosporImager.

Thus, specific embodiments and applications of antiviral phosphonate compounds have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A nucleotide analog having a structure according to Formula 1 or Formula 2,

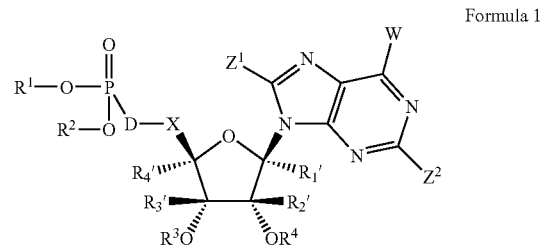

Formula 1

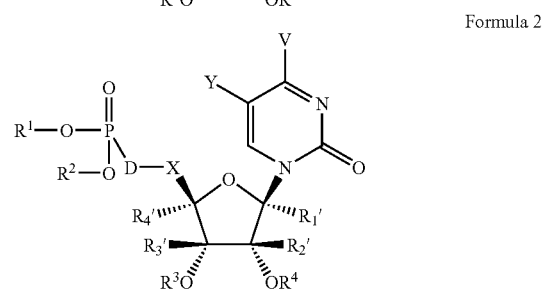

Formula 2 wherein $Z^1$ and $Z^2$ are independently H, alkyl, halogen, $OR^5$, $SR^5$, $NR^5R^6$, CO-alkyl, CO-aryl, or CO-alkoxyalkyl, and wherein W is H, $OR^5$, $SR^5$, $NR^5R^6$, $NH(NR^5R^6)$, $N(alkyl)(NR^5R^6)$, CN, $C(O)NR^5R^6$, $C(NH)NR^5R^6$, or halogen;

wherein V is hydrogen, halogen, $OR^5$, $SR^5$, $NR^5R^6$, $NH(NR^5R^6)$, $N(alkyl)(NR^5R^6)$, CN, $C(O)NR^5R^6$, or $C(NH)NR^5R^6$, and wherein Y is H, alkyl, halogen, $OR^5$, $SR^5$, $NR^5R^6$, CO-alkyl, CO-aryl, or CO-alkoxyalkyl;

X is a covalent bond between the C4'-atom of the sugar and the carbon atom in the phosphonate group, O, $CH_2$, $CHR^5$, CHHalogen, or $C(Halogen)_2$;

D is $CH_2$, CHHalogen, or $C(Halogen)_2$;

$R^1$ $R^2$ are independently H, or phosphate;

$R_1'$, $R_2'$, $R_3'$, and $R_4'$ are independently H or alkyl, with the proviso that at least one of $R_1'$, $R_2'$, $R_3'$, and $R_4'$ is alkyl;

$R^3$ and $R^4$ are independently H, phosphate, acyl, or alkyl;

$R^5$ and $R^6$ are independently H, alkyl, or acyl.

2. The nucleotide analog of claim 1 wherein the nucleotide analog has a structure according to Formula 1.

3. The nucleotide analog of claim 1 wherein X is a covalent bond between the C4'-atom of the sugar and the carbon atom in the phosphonate group, O, or $CH_2$, and wherein at least one of $R_1'R_2'R_3'$, and $R_4'$ is $CH_3$.

4. The nucleotide analog of claim 3 wherein $R_2'$ is $CH_3$.

5. The nucleotide analog of claim 3 wherein $Z_1$ and $Z_2$ are H, and wherein W is $NR^5R^6$.

6. The nucleotide analog of claim 1 wherein the nucleotide analog has a structure according to Formula 2.

7. The nucleotide analog of claim 6 wherein X is a covalent bond between the C4'-atom of the sugar and the carbon atom in the phosphonate group, O, or $CH_2$, and wherein at least one of $R_1$, $R_2'$, $R_3'$, and $R_4'$ is $CH_3$.

8. The nucleotide analog of claim 7 wherein $R_2'$ is $CH_3$.

9. The nucleotide analog of claim 7 wherein Y is H or $CH_3$, and wherein V is OH or $NR^5R^6$.

10. A prodrug of a nucleotide analog having a structure according to Formula 3 or Formula 4,

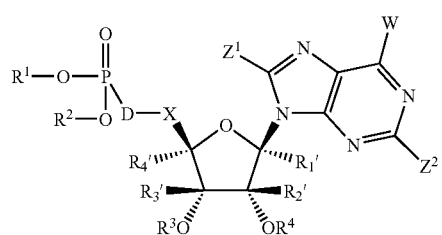

Formula 1

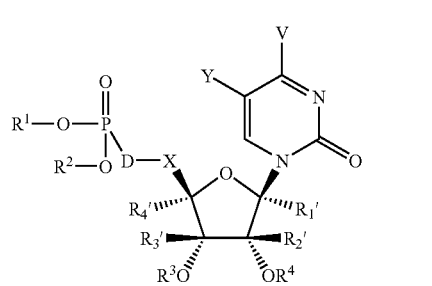

Formula 2 wherein $Z^1$ and $Z^2$ are independently H, alkyl, halogen, $OR^5$, $SR^5$, $NR^5R^6$, CO-alkyl, CO-aryl, or CO-alkoxyalkyl, and wherein W is H, $OR^5$, $SR^5$, $NR^5R^6$, $NH(NR^5R^6)$, $N(alkyl)(NR^5R^6)$, CN, $C(O)NR^5R^6$, $C(NH)NR^5R^6$, or halogen;

wherein V is hydrogen, halogen, $OR^5$, $SR^5$, $NR^5R^6$, $NH(NR^5R^6)$, $N(alkyl)(NR^5R^6)$, CN, $C(O)NR^5R^6$, or $C(NH)NR^5R^6$, and wherein Y is H, alkyl, halogen, $OR^5$, $SR^5$, $NR^5R^6$, CO-alkyl, CO-aryl, or CO-alkoxyalkyl;

X is a covalent bond between the C4'-atom of the sugar and the carbon atom in the phosphonate group, O, $CH_2$, $CHR^5$, CHHalogen, or $C(Halogen)_2$;

D is $CH_2$ CHHalogen, or C $(Halogen)_2$;

$R_1'$, $R_2'$, $R_3'$, and $R_4'$ are independently H or alkyl, with the proviso that at least one of $R_1'$, $R_2'$, $R_3'$, and $R_4'$ is alkyl:

$R^3$ and $R^4$ are independently H, phosphate, acyl, or alkyl;

$R^5$ and $R^6$ are independently H, alkyl, or acyl;

$R^1$ and $R^2$ together are

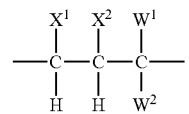

wherein:

$X^1$, $W^1$, and $W^2$ are independently selected from the group consisting of H, alkyl, aralkyl, alicyclic, aryl, substituted aryl, heteroaryl, substituted heteroaryl, 1-alkenyl, and 1-alkynyl; or together $X^1$ and $X^2$ are connected via an additional 3-5 atoms to form a cyclic group containing 5-7 atoms, optionally 1 heteroatom, substituted with hydroxy, acyloxy, alkoxycarbonyloxy, or aryloxycarbonyloxy attached to a carbon atom that is three atoms from both O groups attached to the phosphorous; or together $X^1$ and $X^2$ are connected via an additional 3-5 atoms to form a cyclic group, optionally containing 1 heteroatom that is fused to an aryl group at the beta and gamma position to the O attached to the phosphorous; or together $X^1$ and $W^1$ are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from an O attached to the phosphorous; or together $X^2$ and $W^1$ are connected via an additional 3-5 atoms to form a cyclic group, optionally containing one heteroatom, and $X^1$ must be aryl, substituted aryl, heteroaryl, or substituted heteroaryl; or together $W^1$ and $W^2$ are connected via an additional 2-5 atoms to form a cyclic group, optionally containing 0-2 heteroatoms, and $X^1$ must be aryl, substituted aryl, heteroaryl, or substituted heteroaryl; wherein $X^2$ is selected from the group consisting of $-CHR^{12}OH$, $-CHR^{12}OC(O)R^{13}$, $-CHR^{12}OC(S)R^{13}$, $-CHR^{12}OC(S)OR^{13}$, $-CHR^{12}OC(O)SR^{13}$, $-CHR^{12}OCO_2R^{13}$, $-OR^{12}$, $SR^{12}$, $-CHR^{12}N_3$, $-CH_2aryl$, $-CH(aryl)OH$, $-CH(CH=CR^{12}{}_2)OH$, $-CH(C\equiv CR^{12})OH$, $-R^{12}$, $-NR^{12}{}_2$, $-OCOR^{13}$, $-OCO_2R^{13}$, $-SCOR^{13}$, $-SCO_2R^{13}$, $-NHCOR^{12}$, $-NHCO_2R^{13}$, $-CH_2NHaryl$, $-(CH_2)_p-OR^{14}$, and $-(CH_2)_p-SR^{14}$;

p is 2 or 3;

$R^{12}$ is selected from the group consisting of $R^{13}$ and —H;

$R^{13}$ is selected from the group consisting of alkyl, aryl, alicyclic, and aralkyl; and $R^{14}$ is selected from the group consisting of —H and lower acyl.

11. The nucleotide analog or prodrug of any of claims 1, 2, 6, or 10, wherein $R_1'$, $R_2'$, $R_3'$, and $R_1'$ are independently H or methyl, provided that at least one of $R_1'$, $R_2'$, $R_3$ and $R_4'$ is methyl.

12. The nucleotide analog or prodrug of 11, wherein only one of $R_1'$, $R_2'$, $R_3'$, and $R_4'$ is methyl.

13. A pharmaceutical composition comprising a nucleotide analog or prodrug according to any one of claims 1, 2, 6, or 10, or a pharmaceutically acceptable salt thereof and a pharmaceutically acceptable carrier.

14. A pharmaceutical composition comprising a nucleotide analog or prodrug according to claim 12, or a pharmaceutically acceptable salt thereof; and a pharmaceutically acceptable carrier.

15. A method of treating a hepatitis C infection in a human, comprising administering to said human an effective amount of a nucleotide analog or prodrug according to any one of claims 1, 2, 6, or 10, or a pharmaceutically acceptable salt thereof.

16. A method of treating a hepatitis C infection in a human, comprising administering to said human an effective amount of a nucleotide analog or prodrug according to claim 12, or a pharmaceutically acceptable salt thereof.

* * * * *